(12) United States Patent
Hamon et al.

(10) Patent No.: US 7,163,803 B2
(45) Date of Patent: *Jan. 16, 2007

(54) METHOD FOR CHARACTERIZING POLYPEPTIDES

(75) Inventors: Christian Hamon, Frankfurt am Main (DE); Andrew Thompson, Cambridge (GB); Thomas Neumann, Frankfurt am Main (DE); Robert Johnstone, Bebington (GB); Abdul Karim Abed Mohammed, Liverpool (GB)

(73) Assignee: Electrophoretics Limited, Surrey (GB)

( * ) Notice: Subject to any disclaimer, the term of this patent is extended or adjusted under 35 U.S.C. 154(b) by 0 days.

This patent is subject to a terminal disclaimer.

(21) Appl. No.: 10/479,843

(22) PCT Filed: Jun. 7, 2002

(86) PCT No.: PCT/GB02/02605

§ 371 (c)(1),
(2), (4) Date: Oct. 13, 2004

(87) PCT Pub. No.: WO02/099435

PCT Pub. Date: Dec. 12, 2002

(65) Prior Publication Data

US 2005/0095661 A1 May 5, 2005

(30) Foreign Application Priority Data

Jun. 7, 2001 (EP) ................ 013049754
Aug. 10, 2001 (EP) ................ 013068424
Feb. 4, 2002 (EP) ................ 022507404

(51) Int. Cl.
*C12Q 1/37* (2006.01)

(52) U.S. Cl. ..................... 435/24; 436/89
(58) Field of Classification Search ........... 435/24; 436/89

See application file for complete search history.

(56) References Cited

U.S. PATENT DOCUMENTS

| | | | |
|---|---|---|---|
| 5,141,474 A | 8/1992 | Fujimoto | |
| 5,750,360 A * | 5/1998 | Fesus et al. | 435/23 |
| 6,156,527 A | 12/2000 | Schmidt et al. | |
| 6,846,679 B1 * | 1/2005 | Schmidt et al. | 436/89 |
| 2005/0042676 A1 * | 2/2005 | Hamon et al. | 435/7.1 |
| 2005/0042713 A1 * | 2/2005 | Thompson et al. | 435/68.1 |

FOREIGN PATENT DOCUMENTS

| | | |
|---|---|---|
| DE | 43 44 425 A1 | 6/1994 |
| EP | 0 333 587 A2 | 9/1989 |
| EP | 0 594 164 A1 | 4/1994 |
| JP | 07-165789 | 6/1995 |
| WO | WO 00/20870 | 4/2000 |
| WO | WO 00/20870 A1 * | 4/2000 |
| WO | WO 01/74842 | 10/2001 |
| WO | WO 01/74842 A1 * | 10/2001 |
| WO | WO 02/08767 | 1/2002 |
| WO | WO 02/08767 A2 * | 1/2002 |

OTHER PUBLICATIONS

D.J.C. Pappin et al., "Rapid Identification of Proteins by Peptide-Mass Fingerprinting"; Current Biology, vol. 3, No. 6, pp. 327-332, 1993.

Matthias Mann et al., "Use of Mass Spectrometric Molecular Weight Information to Identify Proteins in Sequence Databases", Biological Mass Spectrometry, vol. 22, pp. 338-345, 1993.

John R. Yates III et al., "Peptide Mass Maps: A Highly Informative Approach to Protein Identification", Analytical Biochemistry, vol. 214, pp. 397-408, 1993.

Eberhard Krause et al., "The Dominance of Arginine-Containing Peptides in Maldi-Derived Tryptic Mass Fingerprints of Proteins", Anal. Chem., vol. 71, pp. 4160-4165, 1999.

Valentina Bonetto et al., "C-Terminal Sequence Determination of Modified Peptides by Maldi MS", Journal of Protein Chemistry, vol. 16, No. 5 pp. 371-374, 1997.

Francesco L. Brancia et al., "A Combination of Chemical Derivatisation and Improved Bioinformatic Tools Optimises Protein Identification for Proteomics", Electrophoresis, vol. 22, pp. 552-559, 2001.

Ruth A. VanBogelen et al., "Application of Two-Dimensional Protein Gels in Biotechnology", Biotechnology Annual Review, vol. 1, pp. 69-103, 1995.

Peter Jungblut et al., "Protein Identification From 2-DE Gels by Maldi Mass Spectrometry", Mass Spectrometry Reviews, vol. 16, pp. 145-162, 1997.

A. Bagree et al., "Modification of ε-Amino Group of Lysine in Proteins by Acylation with Pyromellitic Dianhydride and o-Sulphobenzoic Anhydride", Febs Letters, vol. 120, No. 2, pp. 275-277, Nov. 1980.

Enrique Palacian et al., "Dicarboxylic Acid Anhydrides as Dissociating Agents of Protein-Containing Structures", Molecular and Cellular Biochemistry, vol. 97, pp. 101-111, 1990.

(Continued)

*Primary Examiner*—Ralph Gitomer
(74) *Attorney, Agent, or Firm*—Buchanan, Ingersoll & Rooney, P.C.

(57) ABSTRACT

Provided is a method for characterizing a polypeptide, which method comprises the steps of: (a) optionally reducing cysteine disulphide bridges in the polypeptide to form free thiols, and capping the free thiols; (b) cleaving the polypeptide with a sequence specific cleavage reagent to form peptide fragments; (c) optionally deactivating the cleavage reagent; (d) capping one or more ε-amino groups that are present with a lysine reactive agent; (e) analyzing peptide fragments by mass spectrometry to form a mass fingerprint for the polypeptide; and (f) determining the identity of the polypeptide from the mass fingerprint.

22 Claims, 10 Drawing Sheets

OTHER PUBLICATIONS

Mendel Friedman et al., "Additive Linear Free-Energy Relationships in Reaction Kinetics of Amino Groups with α,β-Unsaturated Compounds", Journal of Organic Chemistry, vol. 31, pp. 2888-2894, 1966.

Margherita Morpurgo et al., "Preparation and Characterization of Poly(Ethylene Glycol) Vinyl Sulfone", Bioconjugate Chem., vol. 7, pp. 363-368, 1996.

Mendel Friedman et al., "Reactions of Proteins with Ethyl Vinyl Sulfone:", Int. J. Peptide Protein Res., vol. 7, pp. 481-486, 1975.

M. Sid Masri et al., "Protein Reactions With Methyl and Ethyl Vinyl Sulfones", Journal of Protein Chemistry, vol. 7, No. 1, pp. 49-54, 1988.

Lila Graham et al., "[$^{14}$C]Acrylonitrile: Preparation Via a Stable Tosylate Intermediate and Quantitative Reaction With Amine Residues in Collagen", Analytical Biochemistry, vol. 153, pp. 354-358, 1986.

Hermann Esterbauer et al., "Reaction of Glutathione With Conjugated Carbonyls", Z. Naturforsch. [C], vol. 30, No. 4, pp. 466-473, 1975.

Mark L. Stolowitz et al., "Phenylboronic Acid-Salicyhydroxamic Acid Bioconjugates. 1. A Novel Boronic Acid Complex for Protein Immobilization", Bioconjugate Chem., vol. 12, pp. 229-239, 2001.

Jean P. Wiley et al., "Phenylboronic Acid-Salicylhydroxamic Acid Bioconjugates. 2. Polyvalent Immobilization of Protein Ligands for Affinity Chromatography", Bioconjugate Chem., vol. 12, pp. 240-250, 2001.

Nigel S. Simpkins, "Tetrahedron Report No. 282", Tetrahedron, vol. 46, No. 20, pp. 6951-6984, 1990.

P. L. Fuchs et al., "Multiply Convergent Syntheses via Conjugate-Addition Reactions to Cycloalkenyl Sulfones", Chem. Rev., vol. 86, pp. 903-917, 1986.

Hiroyasu Tsuge et al., "Regio- and Sterio-Selective Synthesis of Trifluoromethylated Isoxazolidines by 1,3-Dipolar Cycloaddition of 1,1,1-Trifluoro-3-Phenylsulfonylpropene With Nitrones, and Their Conversion Into Trifluoromethylated Syn-3-Amino Alcohols", J. Chem. Soc. Perkin Trans, vol. 1, pp. 2761-2766, 1995.

Norman E. Sharpless et al., "The Reactions of Amines and Amino Acids With Maleimides. Structure of the Reaction Products Deduced From Infrared and Nuclear Magnetic Resonance Spectroscopy", Biochemistry, vol. 5, No. 9, pp. 2963-2971, 1966.

A. Papini et al, "Alkylation of Histidine With Maleimido-Compounds", Int. J. Peptide Protein Res., vol. 39, pp. 348-355, 1992.

M. Niyaz Khan, "Kinetics and Mechanism of the Alkaline Hydrolysis of Maleimide", Journal of Pharmaceutical Sciences, vol. 73, No. 12, pp. 1767-1771, Dec. 1984.

Peter C. Jocelyn, "[46] Chemical Reduction of Disulfides", Methods in Enzymology, vol. 143, pp. 246-256, 1987.

L. H. Krull et al., "2-Vinylquinoline, a Reagent to Determine Protein Sulfhydryl Groups Spectrophotometrically", Analytical Biochemistry, vol. 40, pp. 80-85, 1971.

M. S. Masri et al., "p-Nitrostyrene: New Alkylating Agent for Sulfhydryl Groups in Reduced Soluble Proteins and Keratins", Biochemical and Biophysical Research Communications, vol. 47, No. 6, pp. 1408-1413, 1972.

Mendel Friedman et al., "Estimation of the Disulfide Content of Trypsin Inhibitors as S-β-(2-Pyridylethyl)-L-Cysteine", Analytical Biochemistry, vol. 106, pp. 27-34, 1980.

Urs Th. Ruegg et al., "[10] Reductive Cleavage of Cystine Disulfides With Tributylphosphine", Methods in Enzymology, vol. 47, pp. 111-116, 1977.

John a. Burns et al., "Selective Reduction of Disulfides by Tris(2-Carboxyethyl)Phosphine", J. Org. Chem., vol. 56, pp. 2648-2650, 1991.

Robert L. Geahlen et al., "A General Method for Preparation of Peptides Biotinylated at the Carboxy Terminus", Analytical Biochemistry, Vo. 202, pp. 68-70, 1992.

Sesha Natarajan et al., "Site-Specific Biotinylation a Novel Approach and its Application to Endothelin-1 Analogs and Pth-Analog", Int. J. Peptide Protein Res., vol. 40, pp. 567-574, 1992.

Vishwanath R. Lyer et al., "The Transcriptional Program in the Response of Human Fibroblasts to Serum", Science, vol. 283, pp. 83-87, Jan. 1, 1999.

Joachim Klose et al., "Two-Dimensional Electrophoresis of Proteins: An Updated Protocol and Implications for a Functional Analysis of the Genome", Electrophoresis, vol. 16, pp. 1034-1059, 1995.

Craig Gerard "[40] Purification of Glycoproteins", Methods in Enzymology, vol. 182, pp. 529-539, 1990.

Edward A. Bayer et al., "Biocytin Hydrazide—A Selective Label for Sialic Acids, Galactose, and Other Sugars in Glycoconjugates Using Avidin—Biotin Technology", Analytical Biochemistry, vol. 170, pp. 271-281, 1988.

Gary E. Means, "[45] Reductive Alkylation of Amino Groups", Methods Enzymol. vol. 47, pp. 469-478, 1977.

Ivan Rayment, "[12] Reductive Alkylation of Lysine Residues to Alter Crystallization Properties of Proteins", Methods in Enzymology, vol. 276, pp. 171-179, 1997.

Raymond Frackelton, Jr. et a., [8] Generation of Monoclonal Antibodies Against Phosphotyrosine and Their Use For Affinity Purification of Phosphotyrosine-Containing Proteins, Methods in Enzymology, vol. 201, pp. 79-92, 1991.

Charles F. B. Holmes, "A New Method for the Selective Isolation of Phosphoserine-Containing Peptides", Feb Letters 04633, vol. 215, No. 1, pp. 21-24, May 1987.

Patrick Fadden et al., "Quantitative and Selective Fluorophore Labeling of Phosphoserine on Peptides and Proteins: Characterization at the Attomole Level by Capillary Electrophoresis and Laser-Induced Fluorescence", Analytical Biochemistry, vol. 225, pp. 81-88, 1995.

Yoshiya Oda et al., "Enrichment Analysis of Phoshorylated Proteins as a Tool for Probing the Phosphorproteome", Nature Biotechnology, vol. 19, pp. 379-382; Apr. 2001.

Huilin Zhou et al., "A Systematic Approach to the Analysis of Protein Phosphorylation", Nature Biotechnology, vol. 19, pp. 375-378, Apr. 2001.

Matthew C. Posewitz et al., "Immobilized Gallium(III) Affinity Chromatography of Phosphopeptides", Anal. Chem. vol. 71, pp. 2883-2892, 1999.

Joyce Corey Gibson et al., "[11] Isolation of Apolipoprotein E-Containing Lipoproteins by Immunoaffinity Chromatography", Methods in Enzymology, vol. 129, pp. 186-198, 1986.

Tanya Tadey et al., "Chromatographic Techniques for the Isolation and Purification of Lipoproteins", Journal of Chromatography B, vol. 671, pp. 237-253, 1995.

Avram Hershko et al., "Immunochemical Analysis of the Turnover of Ubiquitin-Protein Conjugates Intact Cells", The Journal of Biological Chemistry, vol. 257, No. 23, pp. 13964-13970, 1982.

Francesco L. Brancia et al., "Improved Matrix-Assisted Laser Desorption/Ionization Mass Spectrometric Analysis of Tryptic Hydrolysates of Proteins Following Guanidination of Lysine-Containing Peptides", Rapid Communications in Mass Spectrometry, vol. 14, pp. 2070-2073, 2000.

Nanying Bian et al., "Detection via Laser Desorption and Mass Spectrometry of Multiplex Electrophore-Labeled Albumin", Rapid Communications in Mass Spectrometry, vol. 11, pp. 1781-1784, 1997.

Samy Abdel-Baky et al., "Gas Chromatography/Electron Capture Negative-Ion Mass Spectrometry at the Zeptomole Level", Anal. Chem. vol. 63, pp. 2986-2989, 1991.

Kenneth D. W. Roth et al., "Charge Derivatization of Peptides for Analysis by Mass Spectrometry", Mass Spectrometry Reviews, vol. 17, pp. 255-274, 1998.

Ronald C. Beavis et al., "Cinnamic Acid Derivatives as Matrices for Ultraviolet Laser Desorption Mass Spectrometry of Proteins", Rapid Communications in Mass Spectrometry, vol. 3, No. 12, 1989.

Farzin Gharahdaghi et al., "Mass Spectrometric Identification of Proteins From Silver-Stained Polyacrylamide Gel: A Method For the Removal of Silver Ions to Enhance Sensitivity", Electrophoresis, vol. 20, pp. 601-605, 1999.

Mary F. Lopez et al., "A Comparison of Silver Stain and Sypro Ruby Protein Gel Stain With Respect to Protein Detection in Two-Dimensional Gels and Identification by Pepetide Mass Profiling", Electrophoresis, vol. 21, pp. 3673-3683, 2000.

Martha M. Vestling et al., "Polyvinylidene Difluoride (PVDF): An Interface for Gel Electrophoresis and Matrix-Assisted Laser Desorption/Ionization Mass Spectrometry", Biochemical Society Transactions, vol. 22, No. 2., pp. 547-551, 1994.

Stephanie Lamer et al., "Matrix-Assisted Laser Desorption-Ionization Mass Spectrometry Peptide Mass Fingerprinting for Proteome Analysis: Identification Efficiency After On-Blot or In-Gel Digestion With and Without Desalting Procedures", Journal of Chromatography B, vol. 752, pp. 311-322, 2001.

Andreas Schlosser et al., Five-Membered Ring Formation in Unimolecular Reactions of Peptides: A Key Structural Element Controlling Low-Energy Collision-Induced Dissociation of Peptides, Journal of Mass Spectrometry, vol. 35, pp. 1382-1390, 2000.

Brenda L. Schwartz et al., "Some Proline Sustituent Effects in the Tandem Mass Spectrum of Protonated Pentaalanine", Biological Mass Spectrometry, vol. 21, pp. 92-96, 1992.

Vicki H. Wysocki et al., "Mobile and Localized Protons: A Framework For Understanding Peptide Dissociation", Journal of Mass Spectrometry, vol. 35, 1399-1406, 2000.

Henri P. Bietlot et al., "Isolation of Carboxyl-Terminal Peptide From Proteins by Diagonal Electrophoresis: Application to the Entomocidal Toxin From Bacillus Thuringiensis", Analytical Biochemistry, vol. 181, pp. 212-215, 1989.

Sjouke Hoving et al., "A Method For the Chemical Generation of N-Terminal Peptide Sequence Tags for Rapid Protein Identification", Anal. Chem., vol. 72, pp. 1006-1014, 2000.

Jeffrey A. Cohn et al., "Chemical Characterization of a Protein-4-Hydroxy-2-Nonenal Cross-Link: Immunochemical Detection in Mitochondria Exposed to Oxidative Stress", Archives of Biochemistry and Biophysics, vol. 328, No. 1, pp. 158-164, Apr. 1, 1996.

* cited by examiner

Pyridyl propenyl sulphonyl biotin

Pyridyl-1-propenyl sulphone

Pyridyl-1-isobutenyl sulphone 3,3,3-trifluoro-1-(pyridylsulphonyl)-1-propene or pyridyl trifluoropropenyl sulphone 2-trifluoromethyl-2-methyl-pyridine-3-vinylsulphone or pyridyl trifluoroisobutenyl sulphone

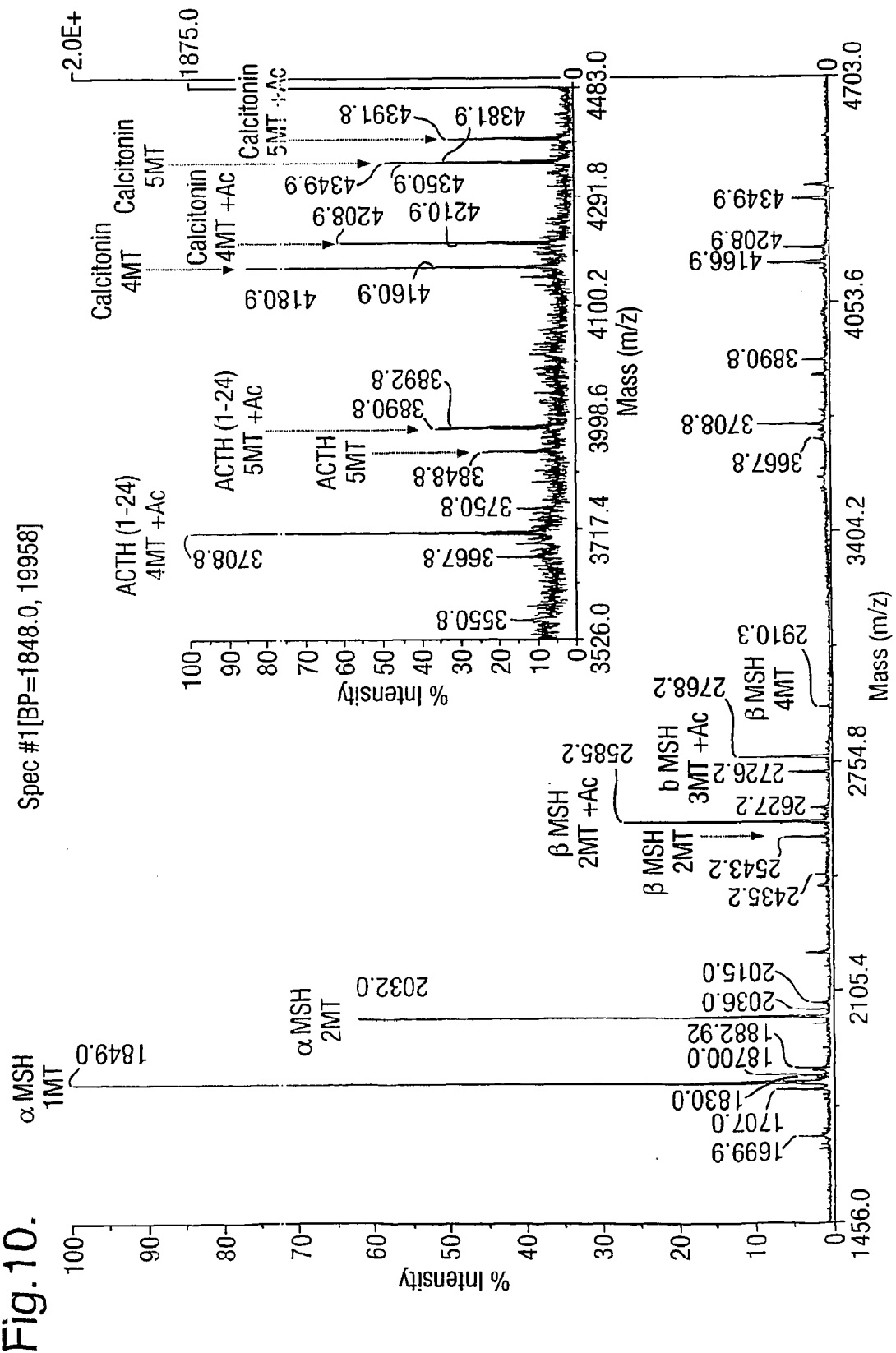

METHOD FOR CHARACTERIZING POLYPEPTIDES

FIELD OF THE INVENTION

This invention relates to methods of determining a mass fingerprint from digests of polypeptides. The invention in particular relates to the use of labels to improve mass fingerprints. This invention further relates to the use of the above methods in determining the expression of proteins in a tissue, cell type, or sub-cellular compartment or in analysing large protein complexes.

BACKGROUND TO THE ART

The identification of proteins in biological samples is an essential activity of biochemical analysis, particularly the determination of the sequence of a protein, since the sequence determines the structure of a protein, which, in turn, determines the function of the protein. Traditional techniques for protein identification are cumbersome and relatively slow. The mainstay of protein identification techniques has been chemical sequencing of peptides using the Edman degradation, which can sequentially identify amino acids in a peptide from the N-terminus. This sequencing technique is typically used in conjunction with enzymatic digestion of a protein or polypeptide. Typically, an unidentified polypeptide is digested and its component peptides are separated from each other by chromatography. The individual peptides are then subjected to Edman degradation. The sequences of the peptides can be ordered by comparing the sequences of peptides from digestion of the polypeptide with different sequence specific cleavage reagents. This process allows the complete sequence of a polypeptide to be determined. While this has been a highly successful technique for the identification of proteins, it is quite laborious.

New technologies have made rapid protein identification more feasible such as Matrix Assisted Laser Desorption Ionisation mass spectrometry.

This technique has permitted the development of peptide mass fingerprinting as a relatively rapid procedure for protein identification.

A typical peptide mass fingerprinting protocol involves determining the mass of the unidentified protein followed by digestion of the protein with trypsin. Trypsin cleaves polypeptides selectively at arginine and lysine residues, leaving either arginine or lysine at the C-termini of the product peptides. The positions of lysine and arginine in the sequence of a polypeptide determine where the polypeptide is cut giving rise to a characteristic series of peptides. The pattern of peptides can be easily detected by MALDI-TOF mass spectrometry. This mass spectrometric technique has a large mass range, can readily ionise large biomolecules, will preferentially produce singly charged ions and competition for ionisation with this technique is not severe, although competition can be problematic. This means that there is generally one peak in the mass spectrum for each peptide, the mass-to-charge ratio for each peak has essentially the same value as the mass of the peptide, with an added proton to ionise the peptide, and most (and sometimes all) the peptides from the digest of an unidentified protein can be analysed simultaneously. In effect the mass spectrum is a 'bar-code' in which the lines in the spectrum represent the masses of the characteristic cleavage peptides of the protein. For any given protein, there may be some peptides, which have the same mass as a peptide from another protein but it is very unlikely that two different proteins will give rise to peptides that all have identical masses. This means that the pattern of masses of the digest of a protein is a fairly unique identifier of that protein and is called a Peptide Mass Fingerprint (PMF). The relative uniqueness of PMFs means that databases of predicted determined from known protein sequences or sequences that have been predicted from DNA or expressed sequence tags (ESTs), can be used to identify proteins in biological samples (Pappin D J C, P and Bleasby A J, Current Biology 3: 327–332, "Rapid identification of proteins by peptide-mass fingerprinting." 1993; Mann M, P, Roepstorff P. Biol Mass Spectrom 22 (6): 338–345, "Use of mass spectrometric molecular weight information to identify proteins in sequence databases." 1993; Yates J R 3rd, Speicher S, Griffin P R, Hunkapiller T, Anal Biochem 214 (2): mass maps: a highly informative approach to protein identification." 1993). The PMF for an unknown protein can be compared with all of the PMFs in a database to find the best match, thereby identifying the protein. Searches of this kind can be constrained by determining the mass of the protein prior to digestion. In this way the pattern of masses of an unidentified polypeptide can be related to its sequence, which in turn can help to determine the role of a protein in a particular sample.

There are, however, many technical difficulties involved in determining the PMF for a protein. A typical protein will give rise to twenty to thirty peptides after cleavage with trypsin, but not all of these peptides will appear in the mass spectrum. The precise reasons for this are not fully understood. One factor that is believed to cause incomplete spectra is competition for protonation during the ionisation process, resulting in preferential ionisation of arginine containing peptides (Krause E. & Wenschuh H. & Jungblut P. R., Anal Chem. 71 (19): 4160–4165, "The dominance of arginine-containing peptides in MALDI-derived mass fingerprints of proteins." 1999). In addition, there are surface effects that result from the process of preparing MALDI targets. The targets are prepared by dissolving the peptide digest in a saturated solution of the matrix material. Small droplets of the peptide/matrix solution are dropped onto a metal target and left to dry. Differences in solubility of peptides will mean that some peptides will preferentially crystallise near the top surface of the matrix where they will be desorbed more readily.

Sensitivity is also a problem with conventional protocols for identifying proteins from their PMF. To be an effective tool, it should be possible to determine a PMF for as small a sample of protein as possible to improve the dynamic range of the analysis of protein samples.

Some attempts have been made to improve the ionisation of peptides that do not contain arginine. Conversion of lysine to homo-arginine is one approach that has met with some success (V. Bonetto et Journal of Protein Chemistry 16 (5): Sequence Determination of Modified Peptides by MALDI MS", 1997; Brancia et al., Electrophoresis 22: 552–559, "A combination of chemical derivitisation and improved tools optimises protein identification for 2001). The conversion of lysine to homo-arginine introduces guanidino functionalities into all of the peptides from a tryptic digest, with the exception of C-terminal peptides, greatly improving the representation of lysine containing peptides in the MALDI-TOF mass spectra.

Conventional techniques for determining the expression of proteins in biological samples depend on protein identification. The goal of protein expression profiling is to identify as many proteins in a sample as possible and, preferably, to determine the quantity of the protein in the sample. A typical method of profiling a population of proteins is by two-dimensional electrophoresis (R. A. Van Bogelen., E. R. Olson, "Application of two-dimensional protein gels in biotechnology.", Biotechnol Annu Rev, 1: 69–103, 1995).

In this method a protein sample extracted from a biological sample is separated by two independent electrophoretic procedures. This first separation usually separates proteins on the basis of their iso-electric point using a gel-filled capillary or gel strip along which a pH gradient exists. Proteins migrate along the gradient until the pH is such that the protein has no net charge, referred to as the iso-electric point, from which the protein can migrate no further. After all of the proteins in the sample have reached their iso-electric point, the proteins are separated further using a second electrophoretic procedure. To perform the second procedure, the entire iso-electric focussing gel strip is then laid against one edge of a rectangular gel. The separated proteins in the strip are then separated in the second gel on the basis of their size. The proteins are thus resolved into a 2-dimensional array of spots in a rectangular slab of acrylamide.

However, after separating the proteins in a sample from each other, there remains the problem of detecting and then identifying the proteins. The currently favoured approach to identify proteins is to analyse the protein in specific spots on the gel by peptide mass fingerprinting using MALDI-TOF mass spectrometry (Jungblut P, Thiede B. "Protein identification from 2-DE gels MALDI mass Spectrom Rev. 16: 145–162, 1997). 2-DE technology is therefore limited by the detection capabilities of the peptide mass fingerprinting methods used in the identification of proteins in gel spots.

The existing technology cannot easily compare the expression levels of two or more samples and there are sensitivity problems with such a complex process due to sample losses during the separation of the proteins and their subsequent recovery from the 2-D gel. In addition, proteins extracted from a 2-D gel are generally in buffers containing solutes that are incompatible with mass spectrometric analysis.

It is an aim of this invention to solve the problems associated with the known methods described above. It is thus an aim of this invention to provide improved methods for producing peptide mass fingerprints, using labels (tags). It is a further aim of this invention to provide methods to determine peptide mass fingerprints using protein reactive reagents that are stable in water, selective for lysine and that work under mild reaction conditions without degradation of the reagents.

SUMMARY OF THE INVENTION

Accordingly, the present invention provides a method for characterising a polypeptide, which method comprises the steps of: (a) optionally reducing cysteine disulphide bridges in the polypeptide to form free thiols, and capping the resulting free thiols; (b) cleaving the polypeptide with a sequence specific cleavage reagent to form peptide fragments; (c) optionally deactivating the cleavage reagent; (d) capping one or more s-amino groups that are present with a lysine reactive agent, preferably a labelled lysine-reactive agent; (e) analysing peptide fragments by mass spectrometry to form a mass fingerprint for the polypeptide; and (f) determining the identity of the polypeptide from the mass fingerprint.

The present invention also provides a method for characterising a population of polypeptides, which method comprises the steps of: (a) optionally reducing cysteine disulphide bridges in one or more polypeptides to form free thiols, and capping the resulting free thiols; (b) separating one or more polypeptides from the population; (c) cleaving one or more polypeptides with a sequence specific cleavage reagent to form peptide fragments; (d) optionally deactivating the cleavage reagent; (e) capping one or more s-amino groups that are present with a lysine reactive agent, preferably a labelled lysine-reactive agent; the peptide fragments by mass spectrometry to form a mass fingerprint for one or more of the polypeptides; and (g) determining the identity of one or more polypeptides from the mass fingerprint.

The present invention also provides a method for comparing a plurality of samples, each sample comprising one or more polypeptides, which method comprises the steps (a) optionally reducing cysteine disulphide bridges and capping the resulting free thiols in one or more polypeptides from the samples; (b) separating one or more polypeptides from each of the samples; cleaving the polypeptides with a sequence specific cleavage reagent to form peptide fragments; (d) optionally deactivating the cleavage reagent; (e) capping one or more s-amino groups that are present with a lysine reactive agent, preferably a labelled lysine-reactive agent; analysing the peptide fragments by mass spectrometry to form a mass fingerprint for one or more polypeptides in the samples; and (g) determining the identity of one or more polypeptides in the samples from one or more mass fingerprints.

BRIEF DESCRIPTION OF THE DRAWINGS

FIG. 10 shows the mass spectrum of an example of a protocol for labelling the alpha-amino groups of a mixture of peptides where both the thiols and epsilon-amino groups of the peptides have already been blocked with the same mass tag.

DETAILED DESCRIPTION OF THE INVENTION

Figure 1:
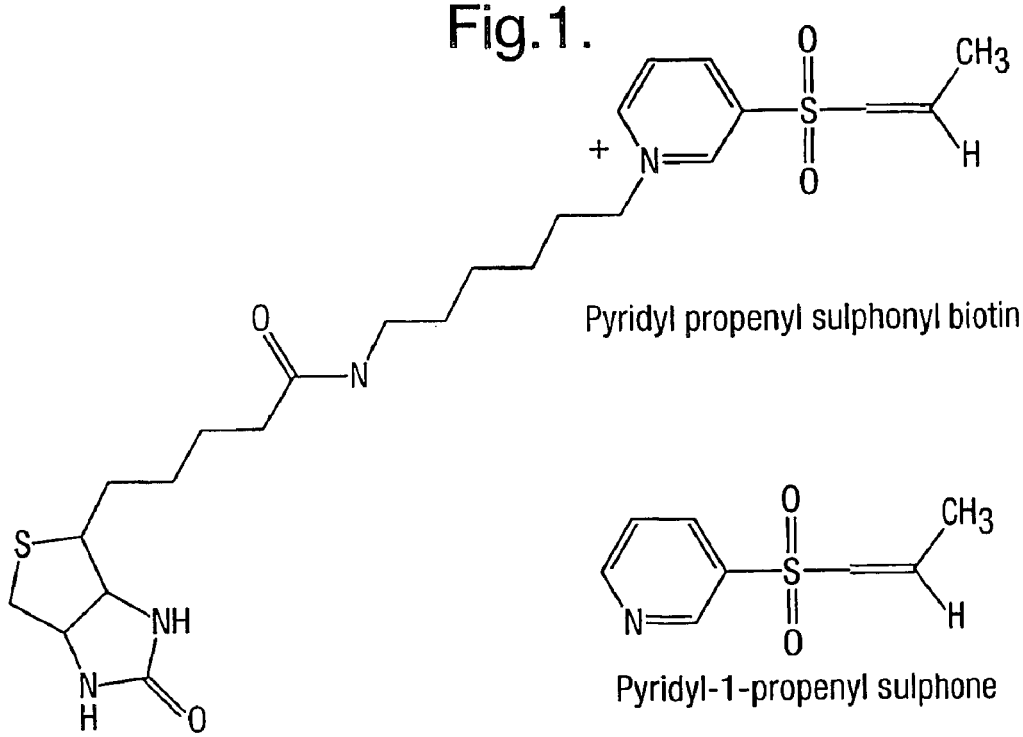
FIG. 1 shows a selection of preferred hindered alkenyl sulphone reagents for use with this invention.
Figure 1:
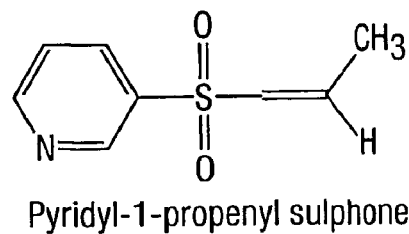
Figure 1:
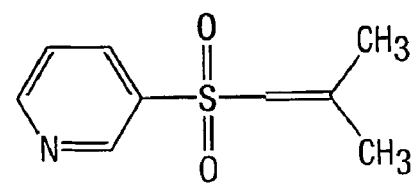
Figure 1:
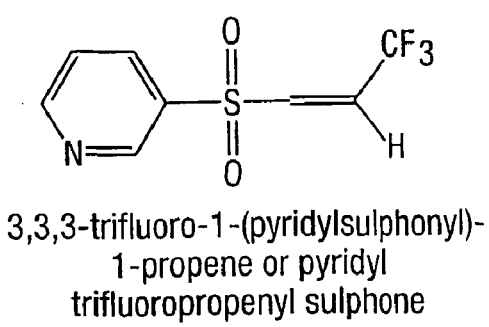
Figure 1:
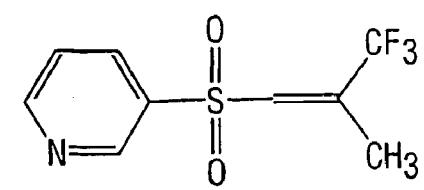

The present invention provides a method for characterising a polypeptide, which method comprises the steps of:

(a) optionally reducing cysteine disulphide bridges in the polypeptide to form free thiols, and capping the resulting free thiols;

(b) cleaving the polypeptide with a sequence specific cleavage reagent to form peptide fragments;

(c) optionally deactivating the cleavage reagent;

(d) capping one or more s-amino groups that are present with a lysine reactive agent, preferably a labelled lysine-reactive agent;

(e) analysing peptide fragments by mass spectrometry to form a mass fingerprint for the polypeptide; and (f) determining the identity of the polypeptide from the mass fingerprint.

The order of the steps as listed above is not intended to represent the order in which the steps must be carried out, and the skilled person will appreciate that the order of some of the steps can be interchanged if desired. Thus, although one preferred order of the non-optional steps is (b), (d), (e) and then (f), another possible order is (d), (b), (e) and then capping step (d) can be carried out before cleaving or after cleaving. For both of these orders, reducing step (a) can be carried out at any time provided that it comes prior to the capping step (d). Also for both of these orders deactivating step (c) can be carried out at any time, provided that it comes after the cleaving step (b), but preferably it is carried out directly after cleaving step (b).

It will be appreciated from the above that this method specifically relates to identifying an unknown polypeptide which may be already isolated or may be present in a sample comprising a population of polypeptides.

The present invention also provides a method for characterising a population of polypeptides, which method comprises the steps of:

(a) optionally reducing cysteine disulphide bridges in one or more polypeptides to form free thiols, and capping the resulting free thiols;

(b) separating one or more polypeptides from the population;

(c) cleaving one or more polypeptides with a sequence specific cleavage reagent to form peptide fragments;

(d) optionally deactivating the cleavage reagent;

(e) capping one or more s-amino groups that are present with a lysine reactive agent, preferably a labelled lysine-reactive agent;

(f) the peptide fragments by mass spectrometry to form a mass fingerprint for one or more of the polypeptides; and (g) determining the identity of one or more polypeptides from the mass fingerprint.

The order of the steps as listed above is again not intended to represent the order in which the steps must be carried out, and the skilled person will appreciate that the order of some of the steps can be interchanged if desired. Thus although one preferred order of the non-optional steps is (b), (c), (e), and then (g), other possible orders are (b), (e), (c), and then (g), and also (e), (b), (c), (f) and then (g). Thus, capping step (e) can be carried out before separating and cleaving, after separating and cleaving or even between separating and cleaving. For all of these orders, separating step (b) must be carried out prior to cleaving step (c). Also for all of these orders, reducing step (a) can be carried out at any time provided that it comes prior to the capping step (e). Again for all of these orders deactivating step (d) can be carried out at any time, provided that it comes after the cleaving step (c), but preferably it is carried out directly after cleaving step (c).

It will be appreciated that this method allows the identification of a plurality of polypeptides in a sample and may be employed to determine the full expression profile of a sample, if desired. Alternatively, this method may be employed to assay for a known polypeptide in a sample whose composition is not known. In these aspects the peptide mass fingerprints of the polypeptides in the sample are determined and compared with the peptide mass fingerprint for the known polypeptide or polypeptides to see which ones are present, and preferably to see in what quantity they is present.

The present invention also provides a method for comparing a plurality of samples, each sample comprising one or more polypeptides, which method comprises the steps of:

(a) optionally reducing cysteine disulphide bridges and capping the resulting free thiols in one or more polypeptides from the samples;

(b) separating one or more polypeptides from each of the samples;

(c) cleaving the polypeptides with a sequence specific cleavage reagent to form peptide fragments;

(d) optionally deactivating the cleavage reagent;

(e) capping one or more s-amino groups that are present with a lysine reactive agent, preferably a labelled lysine-reactive agent;

(f) analysing the peptide fragments by mass spectrometry to form a mass fingerprint for one or more polypeptides in the samples; and (g) determining the identity of one or more polypeptides in the samples from one or more mass fingerprints.

The order of the steps as listed above is not intended to represent the order in which the steps must be carried out, and the skilled person will appreciate that the order of some of the steps can be interchanged if desired. Thus although one preferred order of the non-optional steps is (b), (c), (e), and then (g), other possible orders are (b), (c), and then (g), and also (e), (b), (c), and then (g). Thus, capping step (e) can be carried out before separating and cleaving, after separating and cleaving or even between separating and cleaving. For all of these orders, separating step (b) must be carried out prior to cleaving step (c). Also for all of these orders, reducing step (a) can be carried out at any time provided that it comes prior to the capping step (e). Again for all of these orders deactivating step (d) can be carried out at any time, provided that it comes after the cleaving step (c), but preferably it is carried out directly after cleaving step (c).

In this embodiment of the invention, it is preferred that at some stage in the method the samples are pooled to make processing more efficient. If the samples are pooled, they can be resolved by ensuring that the same label is employed for polypeptides or peptides from the same sample, and different labels are employed for polypeptides or peptides from different samples, such that the sample from which a polypeptide or peptide originates can be determined from its label. The labels are preferably introduced in the capping step and are thus preferably attached to the lysine-reactive agent. The pooling step can take place at any time, provided that the samples are individually labelled, as discussed above. Thus, if the labels are introduced during the capping step, pooling must take place after capping to ensure that the samples do not become mixed before the labels have been introduced. Preferably the samples are pooled before the individual proteins are separated so that all the proteins in all the samples are separated at the same time in the same step. This is particularly efficient.

In some cases a particular protein will be present in more than one sample. These proteins will clearly have the same mass fingerprint. If the proteins are not separated, these mass fingerprints will be overlaid after performing mass spectrometry on the cleavage products. However, each fingerprint can be resolved due to the presence of the labels. Therefore, since the identity of the sample from which the protein comes can be resolved, it can be advantageous when comparing two or more samples to identify the same proteins together in the same spectrum to compare their expression levels. Thus, in some embodiments it is preferred that the same proteins from different samples do not become separated. This can be achieved by ensuring that the different labels used for each sample all have the same mass. Labels of this type that can be used in this invention are described in As will be clear from the above-mentioned order of the method steps, generally it is preferred that the polypeptides in a sample are separated before cleavage occurs, since identical fragments may be produced from different polypeptides, which may prevent resolution of the different mass fingerprints in some cases. The cleaving step preferably takes place after separating to avoid fragments from one polypeptide becoming mixed with fragments from other polypeptides. This particularly applies to methods involving a number of samples, since these sample can be more conveniently labelled in the capping step prior to any separation.

The present methods have the advantage of improved sensitivity and can increase the number of peptides that are detected from a protein. In addition, through the use of appropriate tags, it is possible with this invention to analyse multiple samples simultaneously and it is also possible to determine the ratios of corresponding peptides in the different samples. With appropriate labelling procedures, it is also possible to facilitate the conditioning of polypeptide samples for detection by mass spectrometry.

The steps (b) and (d) of the method of the present invention can be carried out in any order, provided that the peptide fragments can be isolated. Thus, in some embodiments the peptides can be cleaved prior to capping, or in other embodiments, the residues can be capped whilst still forming part of a polypeptide, which polypeptide is subsequently cleaved. In the latter embodiments, the cleavage reagent is preferably capable of cleaving on the C-terminal side of lysine residues even after these residues have been capped. The peptide fragments comprising capped s-amino groups are preferably removed by capturing these fragments, e.g. on a solid phase. In this embodiment, the lysine reactive agent is a lysine selective capture agent. Selective capture may be achieved by attaching a capture group to the lysine reactive agent (such as biotin), which ensures that the agent along with its capped peptide fragment attaches to a solid phase (such as an avidinated solid phase) after capping has occurred. In an alternative embodiment, the lysine reactive agent may be attached to a solid phase before the capping takes place, so that the peptide fragments are captured onto the solid phase by the capping reaction itself.

The capped fragments can thus be removed from the sample by separating the sample from the solid phase, leaving the capped fragments separate from the sample on the solid phase. These fragments may then be analysed to determine the polypeptides present in the original sample.

The method of the invention allows lower concentrations of the reagents to be used at higher Both of these factors have been found by the inventors to improve the selectivity and completeness of lysine reactions. In the following description, lysine amino groups will be referred to as epsilon amino groups.

The lysine reactive agent is preferably a hindered Michael reagent. A Michael reagent has a general formula as below:

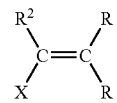

In the above formula, an electron withdrawing group that is capable of stabilising a negative charge. The functional group-X is preferably selected from those listed in Table 1 below:

TABLE 1

| Functional Group | Structure |
| --- | --- |
| Aldehyde | $-\overset{\overset{\displaystyle O}{\|}}{C}-H$ |
| Amide | $-\overset{\overset{\displaystyle O}{\|}}{C}-N\overset{R^1}{\underset{R^2}{}}$ |
| Ester | $-\overset{\overset{\displaystyle O}{\|}}{C}-O-R^1$ |
| Ketone | $-\overset{\overset{\displaystyle O}{\|}}{C}-R^1$ |
| Nitrile | $-C\equiv N$ |
| Pyridine ring | (pyridine ring, 3- or 4-substituted) |
| Sulphone | $-\overset{\overset{\displaystyle O}{\|}}{\underset{\underset{\displaystyle O}{\|}}{S}}-R^1$ |

Where $R^1$ may be any alkyl or aromatic group but is preferably an electron withdrawing group and more preferably a cyclic or heterocylic aromatic ring or fused ring. Preferably the ring structure is electron withdrawing. More specifically RI is preferably a small ring or fused ring such as a phenyl, pyridyl, naphthyl or quinolyl ring structure. Preferred ring structures are substituted with appropriate electron withdrawing groups such as halogens like fluorine or nitro groups. Preferred ring structures promote water solubility, such as pyridyl and naphthyl rings. If-X is an amide, then one or both of the R1 groups may be a hydrogen atom. If-X is a nitrile, preferred compounds include crotonitriles such as $R^1$ may additionally comprise a linker to an affinity capture functionality, such as biotin, or a linker to a solid phase support.

In the formula above $R^2$ is either a hydrogen atom or it may comprise an electron-withdrawing group and/or a linker to an affinity capture functionality or a linker to a solid phase support. Further specific groups that may be are listed below in the definition of the group Sub.

To be a 'hindered' Michael reagent according to this invention, at least one of the R groups is not hydrogen and is considered to be a sterically hindering group. At least one R group may comprise an alkyl or aromatic group such as a methyl or phenyl group. More preferably at least one of the R groups is electron-withdrawing and may comprise a halogen atom or a halogenated alkyl group, such as fluoromethyl, difluoromethyl or trifluoromethyl group or a phenyl ring with electron withdrawing substituents such as halogen or nitro groups. In addition, one R-group may comprise a linker to an affinity capture functionality, such as biotin, or a linker to a solid phase support. Conversely to be an 'unhindered' Michael reagent in the context of this invention, both R groups would be hydrogen.

In a preferred embodiment, one (and more preferably only one) of the X-, R-, $R^1$-and $R^2$-groups comprises a linker to an affinity capture functionality, such as biotin, or a linker to a solid phase support.

In some embodiments, the X group may be joined to one of the R groups to form a ring.

Preferred compounds of this type include of the formula:

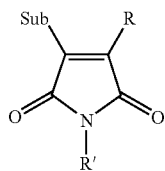

Where R has the same meaning as above and R' is a hydrocarbon group or an electron donating group. Preferably R comprises an alkyl group or aryl group and particularly preferably R comprises a C1–C6 alkyl group, such as a methyl or ethyl group.

The group Sub in the above formulae is not particularly limited, provided that the Michael agent is capable of reacting with an £-amino group. The group is generally a group $R^2$ as defined above, and more specifically in preferred embodiments of the invention, Sub comprises a hydrocarbon group such as an alkyl or aryl group or an electron withdrawing group, such as a cyano group (—CN), or a halogen (F, Br, or halogen-containing group. In the most preferred embodiments, Sub comprises a hydrogen, or a alkyl group, such as a methyl or ethyl group. A particularly preferred compound is one in which Sub and R are both H and R' comprises a methyl group or an ethyl group.

In the context of this invention, the term lysine-selective reagent refers to the ability of the reagent to discriminate between the epsilon-amino group of lysine and the alpha-amino groups of all amino acids. It is also preferred that the reagents of this invention do not react with other side chain such as the imidazole ring of histidine, the guanidino group of arginine and hydroxyl functionalities found in serine, threonine and tyrosine.

In the context of this invention, the term capture reagent refers to the ability of the reagent to capture molecules onto a solid support. Thus, as mentioned above, the capture reagent may comprise a reactive functionality linked covalently to a solid phase support, or it may comprise a reactive functionality linked to functionality that can be chemically linked to a solid phase support or it may comprise a reactive functionality linked to an affinity capture functionality, which can be captured to a solid support by interaction with a specific ligand that is linked to the solid support.

The various aspects of this invention will now be discussed in more detail below.

In one embodiment of this invention there is provided a method of determining a mass fingerprint for a polypeptide comprising the steps 1. Digesting the polypeptide completely with a sequence specific cleavage reagent.
2. Reacting the polypeptide with a lysine reactive hindered Michael reagent so that all available epsilon-amino groups in the polypeptide are capped with the reagent and preferably only one molecule of the alkylating Michael reagent reacts with each epsilon-amine available in the polypeptide.
3. Analysing the labelled peptides from the digested polypeptide by mass spectrometry.

In this and other embodiments of the present invention, a further optional step may also be carried out in case disulphide linkages are present This step involves reducing disulphide linkages in the polypeptides, and capping resultant free thiols (and/or free thiols initially present) in the polypeptides. If desired, this step may be carried out prior to digesting the sample with the cleavage agent, e.g.:

1. Optionally reducing cysteine disulphide bridges and capping of free thiols.
2. Digesting the polypeptide completely with a sequence specific cleavage reagent.
3. Reacting the polypeptide with a lysine reactive hindered Michael reagent so that all available epsilon-amino groups in the polypeptide are capped with the reagent and preferably only one molecule of the alkylating Michael reagent reacts with each epsilon-amine available in the polypeptide.
4. Analysing the labelled peptides from the digested polypeptide by mass spectrometry.

In a further aspect, this invention provides a method for determining the expression profile of a sample, which method comprises characterising a plurality of polypeptides from one or more mixtures of polypeptides according to a methods defined above. Thus, this aspect of the invention provides a method of determining the expression profile of at least one mixture of polypeptides, and is a method to identify and preferably also to quantify each polypeptide in the mixture.

In preferred embodiments of this invention the sequence specific cleavage reagent is Trypsin or Lys-C.

In preferred embodiments of this invention the lysine reactive tag comprises a sensitivity enhancing group. This sensitivity enhancing group improves the ionisation efficiency of the tagged peptides. Preferred sensitivity enhancing groups include non-fluorescent dyes such as cinnamic acid derivatives, tertiary amino groups, guanidino groups, quaternary ammonium groups or pyridinium groups.

In some embodiments of the invention, the lysine reactive tag may comprise an affinity capture agent such as biotin.

In a yet further aspect, this invention provides a lysine selective protein labelling reagent that comprises a thiol and amino reactive hindered alkenyl sulphone compounds with the formula:

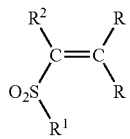

Where $R^1$ may be any alkyl or aromatic group but is preferably an electron withdrawing group and more preferably a cyclic or heterocylic aromatic ring or fused ring. Preferably the ring structure is electron withdrawing. More specifically $R^1$ is preferably a small ring or fused ring such as a phenyl, pyridyl, naphthyl or quinolyl ring structure. Preferred ring structures are substituted with appropriate electron withdrawing groups such as halogens like fluorine or nitro groups. Preferred ring structures promote water solubility, such as pyridyl and naphthyl rings may additionally comprise a linker to an affinity capture functionality, such as biotin, or a linker to a solid phase support.

In the formula above $R^2$ is most preferably a hydrogen atom, but it may alternatively comprise an electron-withdrawing group and/or a linker to an affinity capture functionality or a linker to a solid phase support.

To be a 'hindered' Michael reagent according to this invention, at least one of the R groups is not hydrogen and is considered to be a sterically hindering group. At least one R group may comprise an alkyl or aromatic group such as a methyl or phenyl group. More preferably at least one of the R groups is electron-withdrawing and may comprise a halogen atom or a halogenated alkyl group, such as fluoromethyl, difluoromethyl or trifluoromethyl group or a phenyl ring with electron withdrawing substituents such as halogen or nitro groups. In addition, one R-group may comprise a linker to an affinity capture functionality, such as biotin, or a linker to a solid phase support. Conversely to be an 'unhindered' Michael reagent in the context of this invention, both R groups would be hydrogen.

Preferably one and more preferably, only one of the R1 and groups comprises a linker to an affinity capture functionality, such as biotin, or a linker to a solid phase support.

In a still further aspect, this invention provides a method of comparing the expression levels of polypeptides in two or more biological samples that comprise a mixture of polypeptides by determining a mass fingerprint for the polypeptides. The preferred method comprises the following steps:

1. For each sample of polypeptides, optionally reducing cysteine disulphide bridges and capping of free thiols in all of the polypeptides;

2. Reacting each sample of polypeptides with a lysine reactive hindered Michael reagent so that all available epsilon-amino groups in the polypeptides are capped with the reagent and preferably only one molecule of the alkylating Michael reagent reacts with each epsilon-amine available in the polypeptides. Each sample is labelled with a different tag from every other sample, where the differences between the tags are resolvable by mass spectrometry.

3. Pooling the labelled samples

4. Separating the component polypeptides of the pooled samples so that each different polypeptide may be isolated.

5. Digesting each polypeptide completely with a sequence specific cleavage reagent.

6. Analysing the labelled peptides from the digested polypeptide by mass spectrometry.

Figure 2:
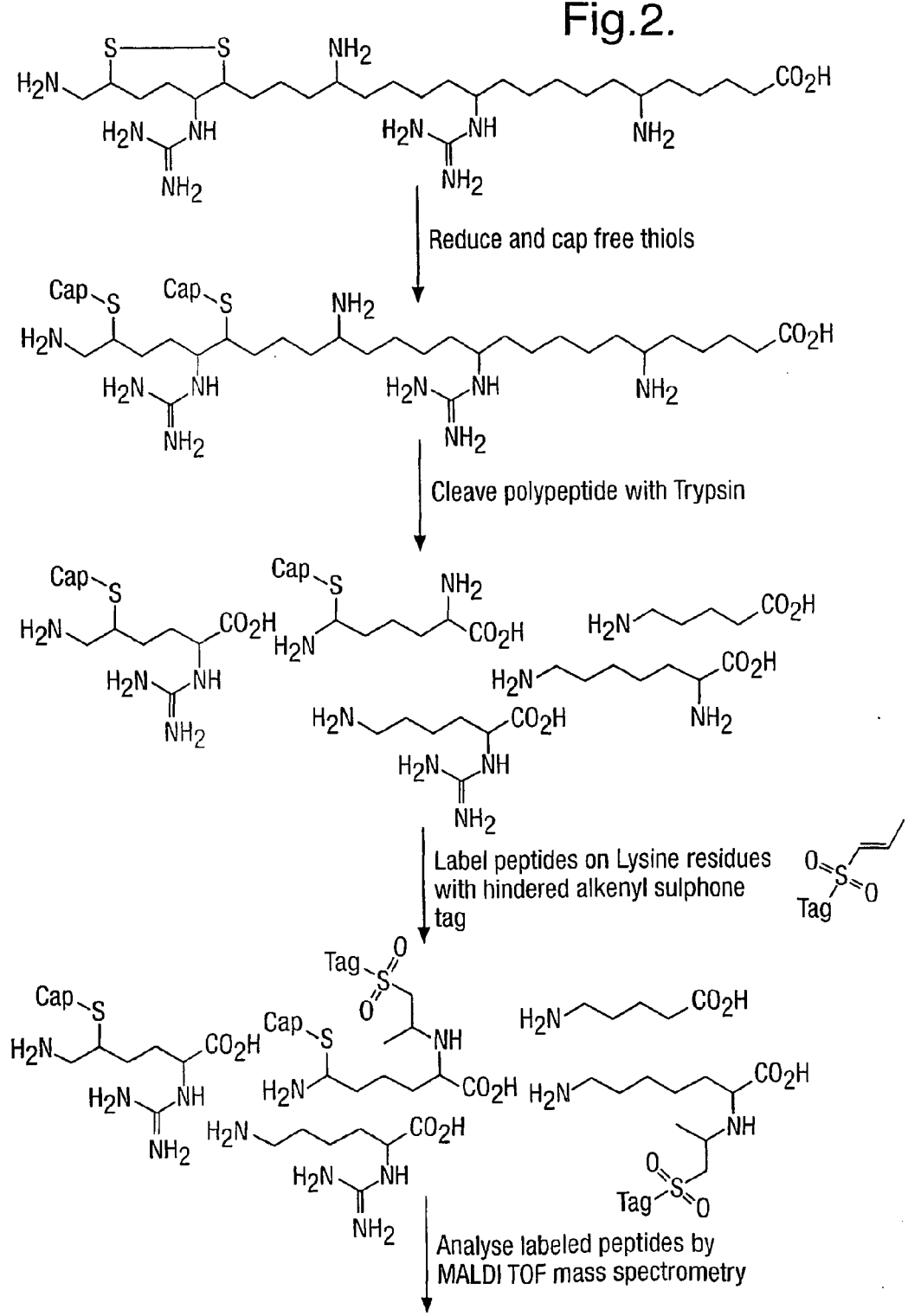
FIG. 2 shows a schematic illustration of the first aspect of this invention in which a polypeptide is prepared for peptide mass fingerprinting using Trypsin as the sequence specific cleavage reagent.
Figure 3:
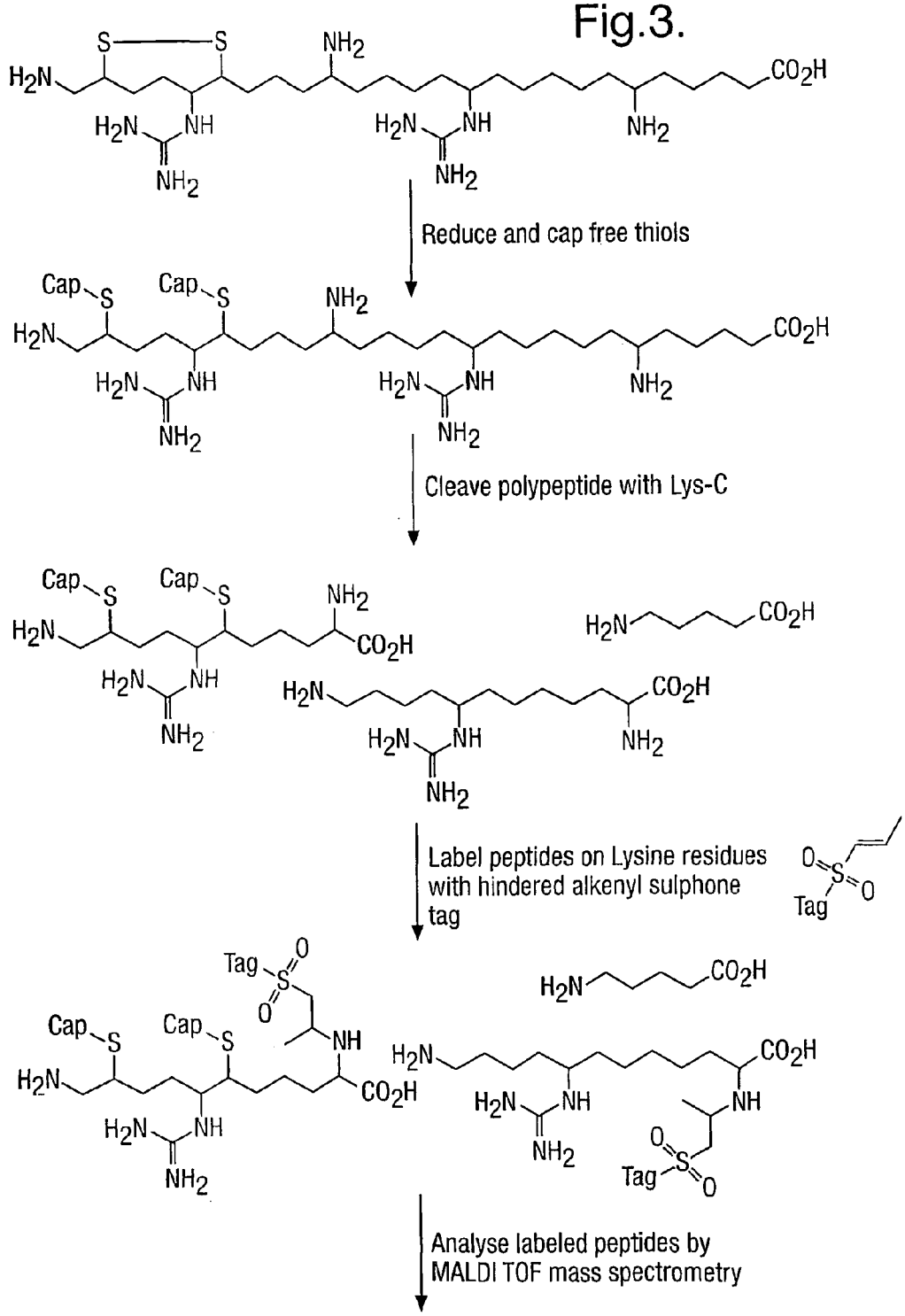
FIG. 3 shows a schematic illustration of the first aspect of this invention in which a polypeptide is prepared for peptide mass fingerprinting using Lys-C as the sequence specific cleavage reagent.
Figure 4:
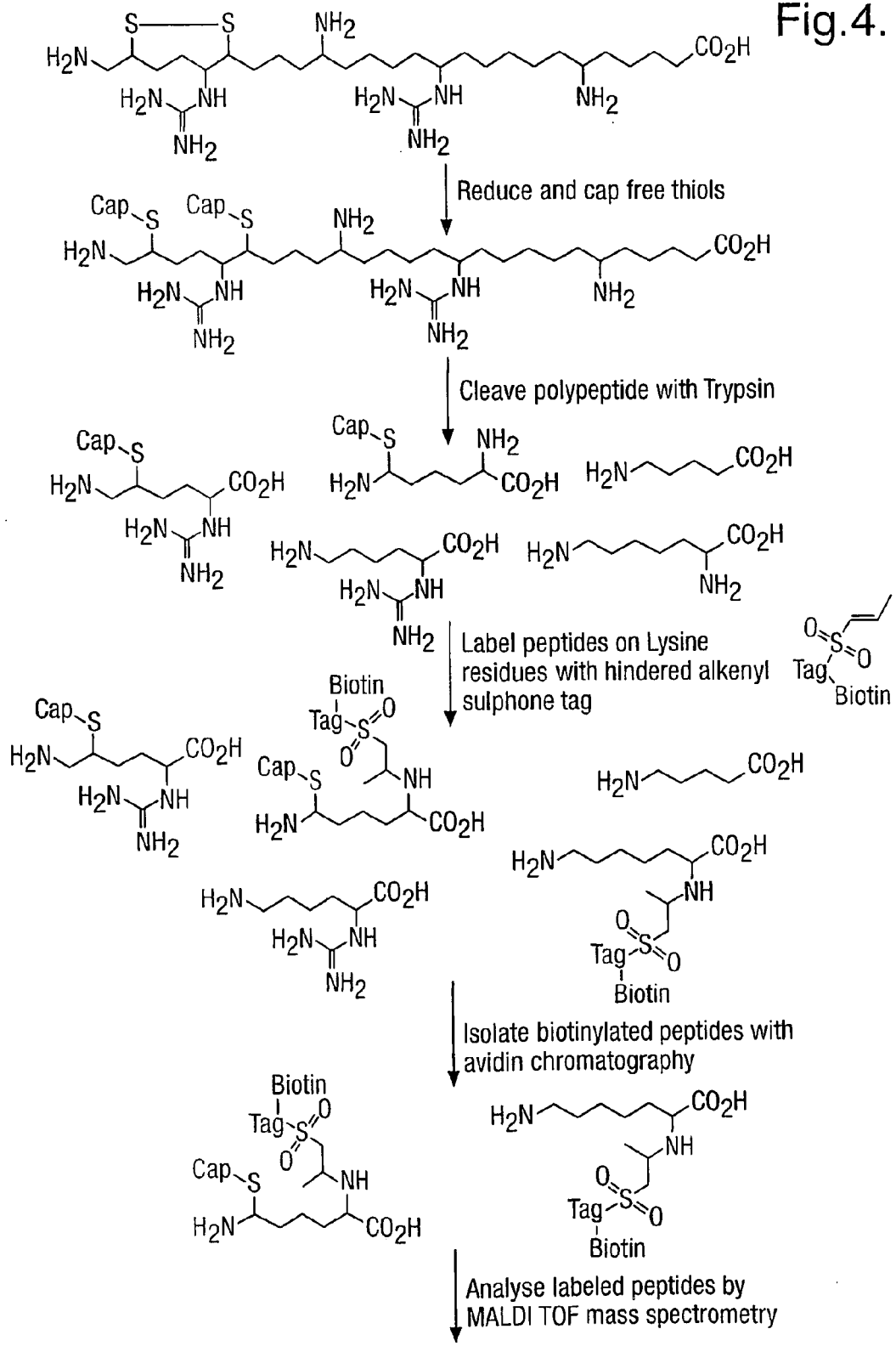
FIG. 4 shows a schematic illustration of the first aspect of this invention in which a polypeptide is prepared for peptide mass fingerprinting using Trypsin as the sequence specific cleavage reagent and a lysine-selective tag that comprises a biotin affinity tag.
Figure 5:
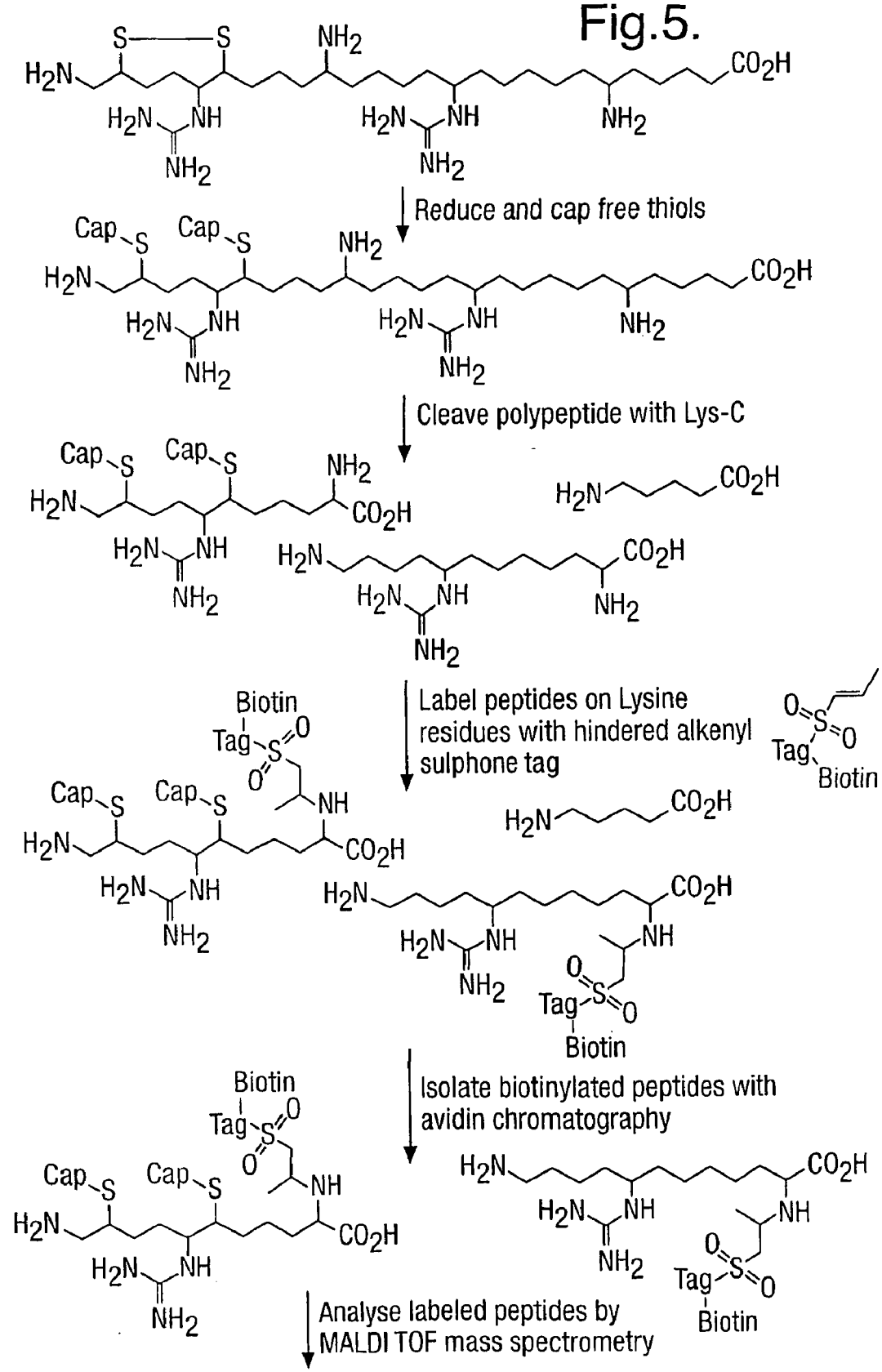
FIG. 5 shows a schematic illustration of the first aspect of this invention in which a polypeptide is prepared for peptide mass fingerprinting using Lys-C as the sequence specific cleavage reagent.
Figure 6:
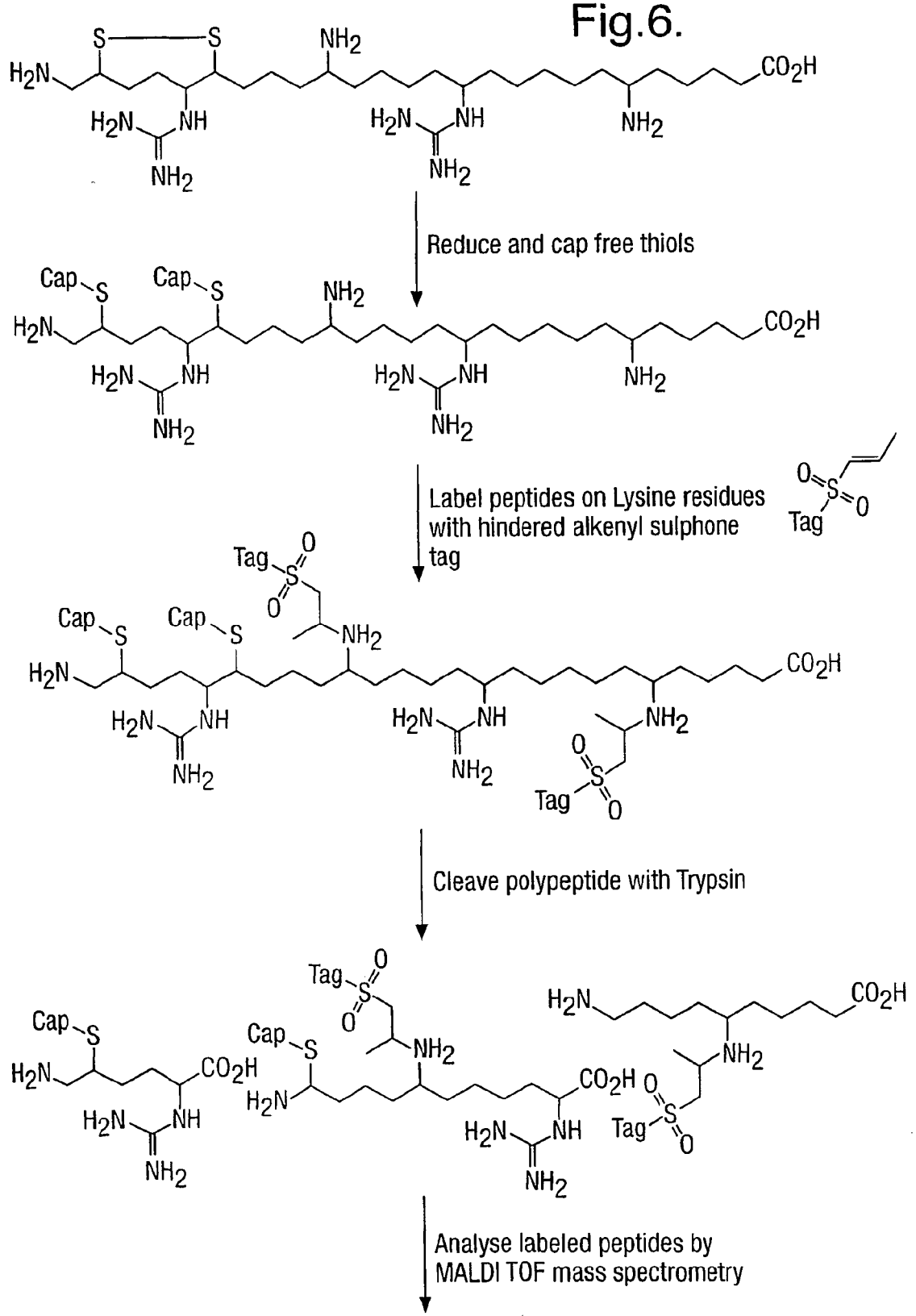
FIG. 6 shows a schematic illustration of the first aspect of this invention in which a polypeptide is prepared for peptide mass fingerprinting using a lysine-selective tag that is reacted with the polypeptide prior to cleavage using Trypsin as the sequence specific cleavage reagent.
Figure 7:
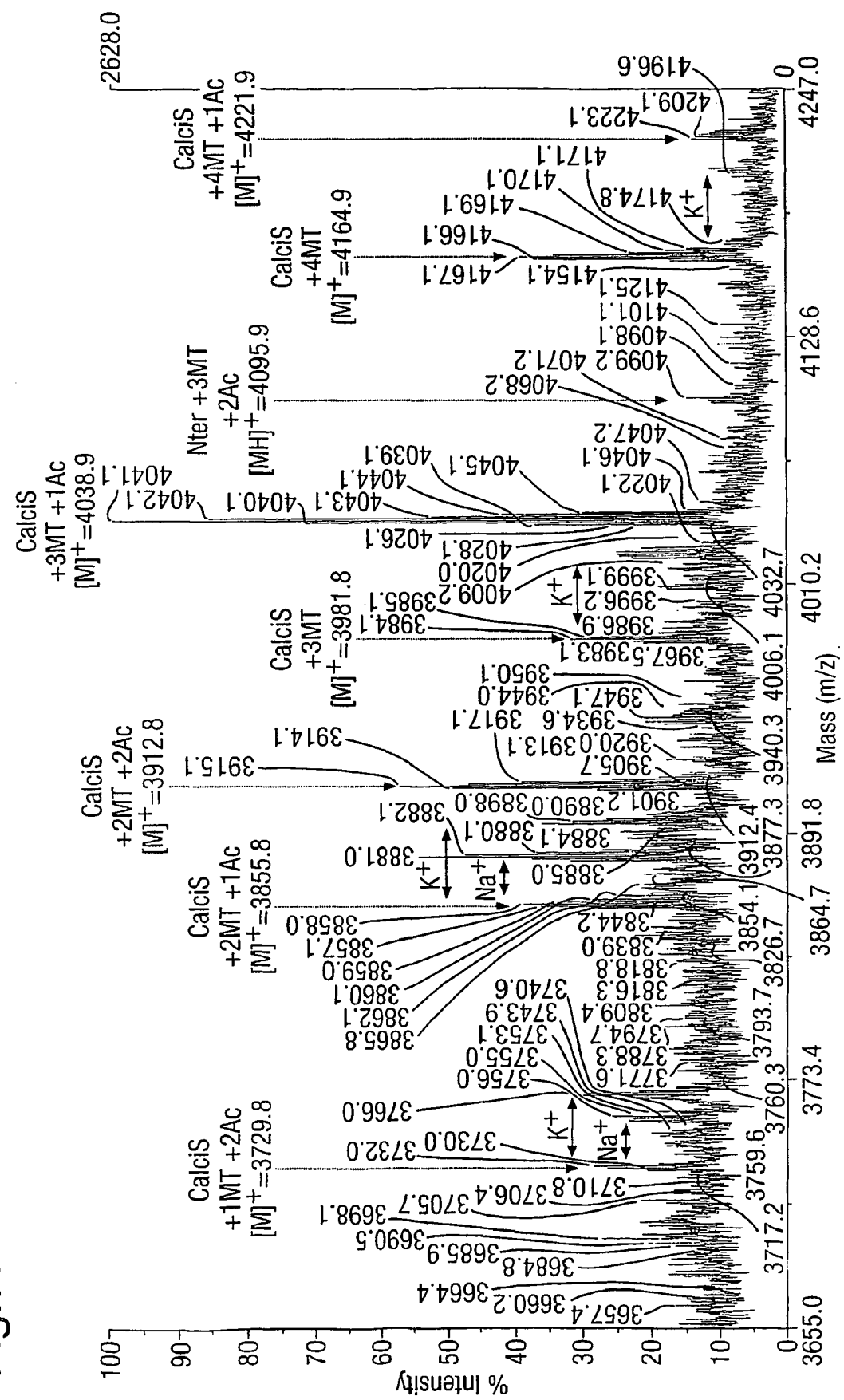
FIG. 7 shows the mass spectrum of an example of a protocol for labelling both the thiols and epsilon amino groups of a peptide.
Figure 8:
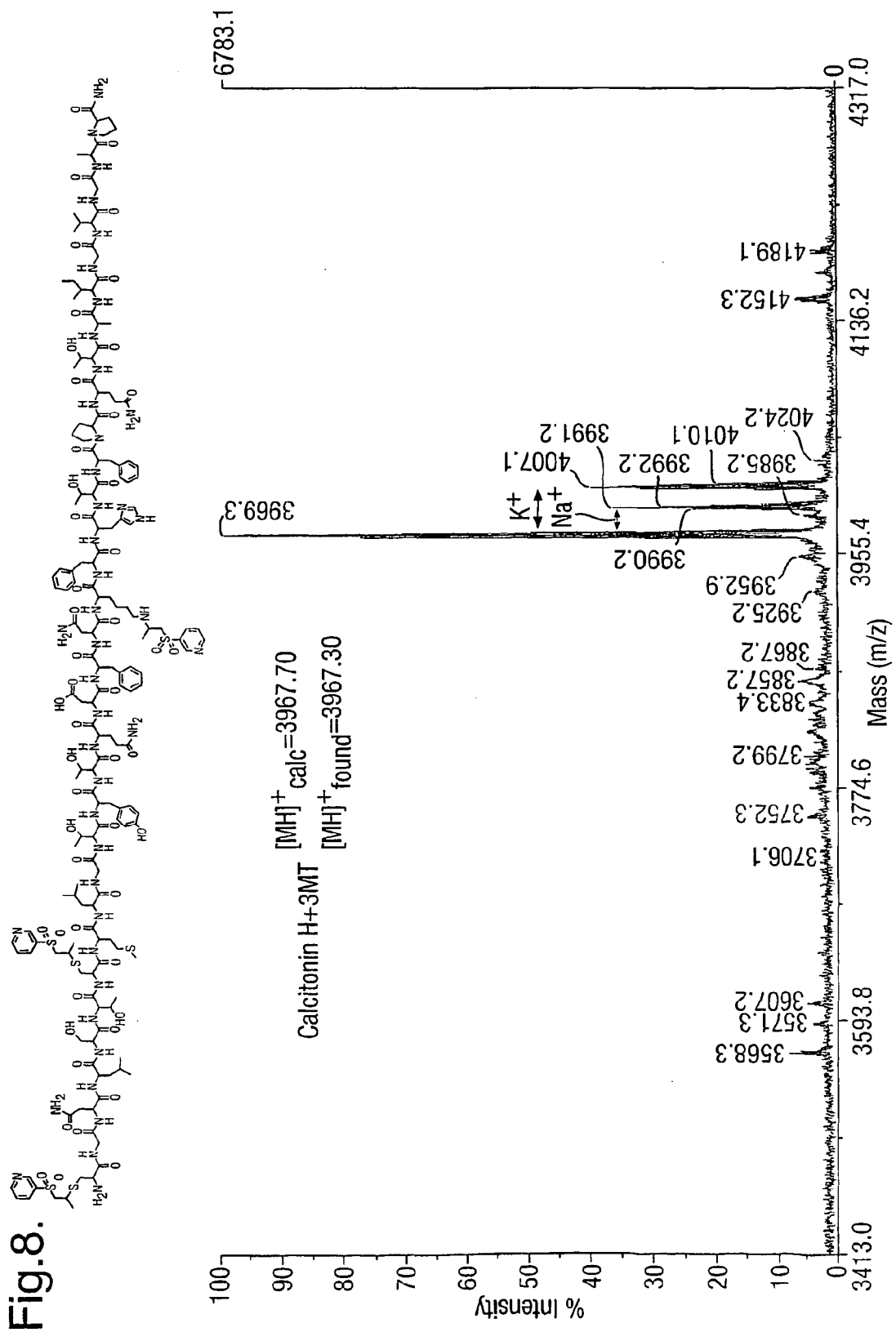
FIG. 8 shows the mass spectrum of an example of a protocol for labelling both the thiols and epsilon amino groups of a peptide with the same label.
Figure 9:
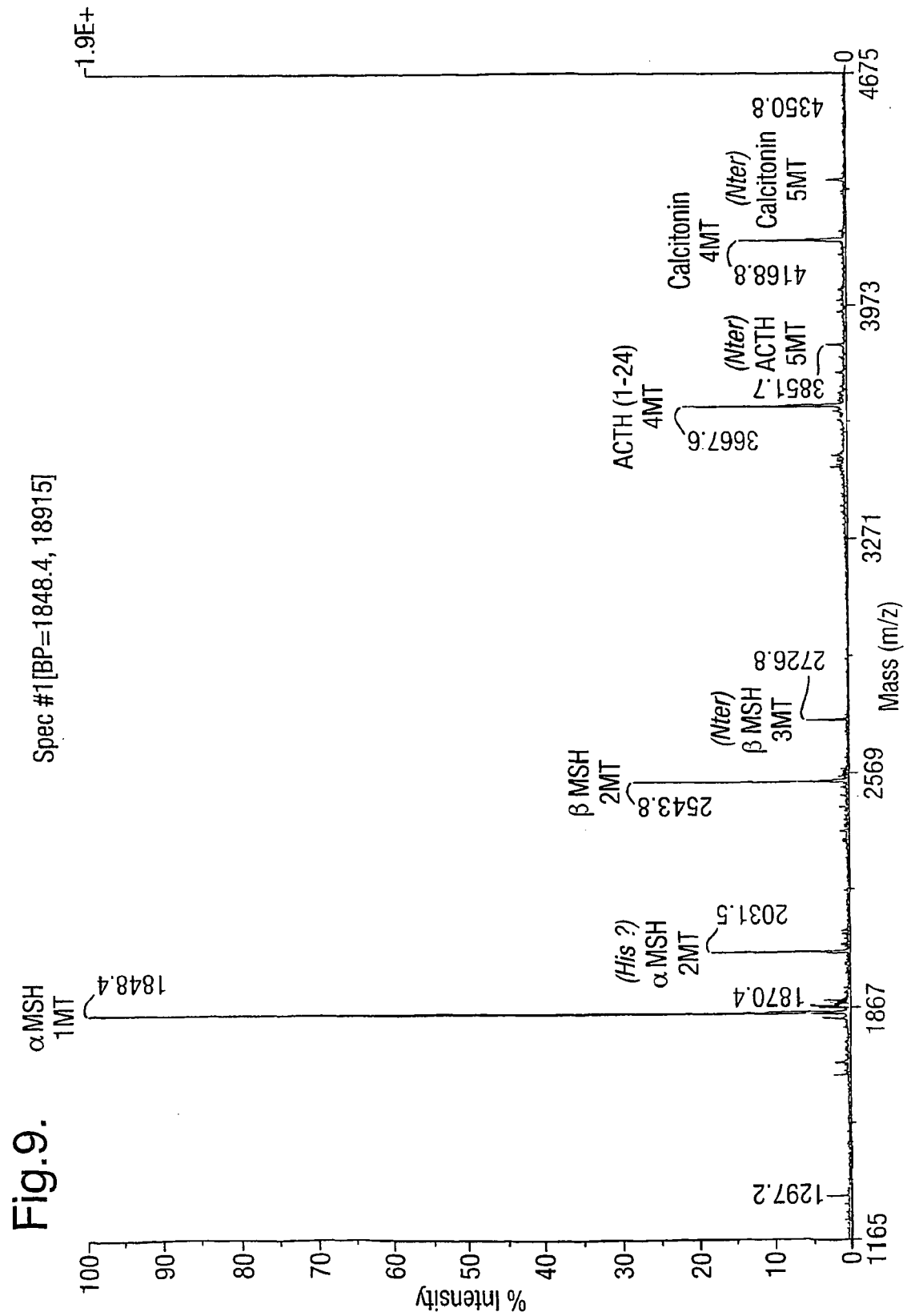
FIG. 9 shows the mass spectrum of an example of a protocol for labelling both the thiols and epsilon amino groups of a mixture of peptides.

The invention will now be described in more detail by way of example only, with reference to the following Figures:

FIG. 1 shows a selection of preferred hindered alkenyl sulphone reagents for use with this invention. Synthetic procedures for the production of some of these reagents is described in the examples section;

FIG. 2 shows a schematic illustration of the first aspect of this invention in which a polypeptide is prepared for peptide mass fingerprinting using Trypsin as the sequence specific cleavage reagent;

FIG. 3 shows a schematic illustration of the first aspect of this invention in which a polypeptide is prepared for peptide mass fingerprinting using Lys-C as the sequence specific cleavage reagent;

FIG. 4 shows a schematic illustration of the first aspect of this invention in which a polypeptide is prepared for peptide mass fingerprinting using Trypsin as the sequence specific cleavage reagent and a lysine-selective tag that comprises a biotin affinity tag;

FIG. 5 shows a schematic illustration of the first aspect of this invention in which a polypeptide is prepared for peptide mass fingerprinting using Lys-C as the sequence specific cleavage reagent;

FIG. 6 shows a schematic illustration of the first aspect of this invention in which a polypeptide is prepared for peptide mass fingerprinting using a lysine-selective tag that is reacted with the polypeptide prior to cleavage using Trypsin as the sequence specific cleavage reagent;

FIG. 7 shows the mass spectrum of an example of a protocol for labelling both the thiols and epsilon amino groups of a peptide. In this example the peptide is Calcitonin S and the thiols are labelled with a different tag from the epsilon amino groups;

FIG. 8 shows the mass spectrum of an example of a protocol for labelling both the thiols and epsilon amino groups of a peptide with the same label;

FIG. 9 shows the mass spectrum of an example of a protocol for labelling both the thiols and epsilon amino groups of a mixture of peptides—in this example the thiols are labelled with the same tag as the epsilon amino groups;

FIG. 10 shows the mass spectrum of an example of a protocol for labelling the alpha-amino groups of a mixture of peptides where both the thiols and epsilon-amino groups of the peptides have already been blocked with the same mass tag;

The lysine reactive (lysine selective) reagents used in the methods of the present invention will now be described in more detail.

Many amine selective protein reactive reagents are known in the art. These reagents will all have some degree of discrimination in favour of reaction with lysine over alpha amino groups at high pH but not many show sufficient discrimination to allow lysine to be labelled almost exclusively. A number of lysine-selective reagents have been described in the prior art and these are all appropriate for use with this invention, particularly cyclic anhydrides. Pyromellitic dianhydride and o-sulphobenzoic acid anhydride are reported to be lysine selective acylating reagents (Bagree et al., FEBS Lett. 120 (2): 275–277, 1980). Similarly Phthalic anhydride, whose structure and reactivity is similar to anhydride would be expected to be lysine selective. Phthalic anhydride is reported to have few side-reactions with other amino acids (Palacian E. et Mol Cell Biochem. 97 (2): 1990). More importantly, most reagents that react with lysine are not stable at high pH, particularly active esters such as carboxylic acid anhydride, N-hydroxysuccinimide esters and pentafluorophenyl esters. These reagents must be used in large excess exacerbating the lack of selectivity of the reaction as a result of the excess.

Michael reagents have a number of properties that make them attractive for protein reactions and have been used quite widely for this purpose (Friedman M. & Wall J. S., J Org Chem 31: 2888–2894, "Additive Linear Free-Energy Relationships in Reaction Kinetics of Amino Groups with alpha, beta-Unsaturated Compounds." 1966; Morpurgo M. & Veronese F. M. & Kachensky D. & Harris J. M., Bioconjug Chem (3): 363–368, "Preparation of characterization of poly(ethylene glycol)vinyl sulfone." 1996; Friedman M. & Finley J. W., Int J Pept Protein Res 7 (6): of proteins with ethyl vinyl sulfone." 1975; Masri M. S. & Friedman M., J Protein Chem 7: 49–54, "Protein reactions with methyl and ethyl vinyl sulfones" 1988; Graham L. & Mechanic G. L., Anal Biochem 153 (2): acrylonitrile: preparation via a stable tosylate intermediate and quantitative reaction with amine residues in collagen." 1986; Esterbauer H. & Zollner & Scholz N., Z Naturforsch [C] 30 (4): of glutathione with conjugated carbonyls." 1975).

There is a number of these reagents that are relatively stable in aqueous solution and the structures of these compounds can be varied extensively to achieve different degrees of reactivity and selectivity. Other reagents used for protein labelling are often not very stable in water and are less easily modified. In particular, reactions with amines are often done with active esters, which are quite susceptible to hydrolysis. Reagents based on sulphones are generally more convenient and effective for labelling amino-groups than the more widely used esters. Michael reagents that have been used with proteins include compounds such as acrylonitrile, acrylamide, vinyl pyridine, methyl vinyl sulphone and methyl vinyl ketone. The reaction of these compounds have been compared (Friedman M. & Wall J. S from above) and linear relationships between the reaction kinetics of these structurally similar compounds are observed. These linear relationships indicate that the reactions of this class of compounds take place by the same mechanism although their rates of reaction differ with the sulphone and ketone compounds found to be by far the most reactive. The vinyl compounds, i.e. acrylonitrile, acrylamide, vinyl pyridine, methyl vinyl sulphone and methyl vinyl ketone have broadly the same relative rates of reaction with different substrates but differ from each other in their overall rates of reaction. These linear relationships make it reasonable to assume that the reactions of this class of compounds take place by the same mechanism and that changes to substituents in this class of compounds, particularly at the beta position of the reactive double bond, will produce similar changes in behaviour in the whole class of compounds. For example, it would be expected that the change in relative reaction rates of crotononitrile with a series of substrates when compared with acrylonitrile would be essentially the same as the change in relative reaction rates of methyl propenyl sulphone with a series of substrates when compared with methyl vinyl sulphone. This means that the properties of methyl propenyl sulphone will be essentially the same as crotononitrile except that the rate of reaction of the sulphone will be faster.

The choice of a Michael reagent for the purposes of this invention is dependent on a number of criteria, included rates of reaction, chances of side-reactions apart from the Michael addition and ease of synthesis of different variants of the compound. Vinyl ketones can, for example, undergo other reactions besides Michael addition, particularly nucleophilic attack of the ketone after Michael addition has taken place. The ketone functionality can undergo this further reaction with a variety of nucleophiles, including the usual biological nucleophiles. Similarly, nitrile compounds can undergo hydrolysis of the nitrile functionality to the carboxylic acid, although typically this reaction will not occur under the conditions used in most biological assays. Alkenyl sulphones do not undergo reactions other than the Michael addition under the conditions used in typical biological assays. Alkenyl sulphones generally react rapidly with biological nucleophiles and there is an extensive literature on the synthesis of different forms of alkenyl sulphone. For these reasons alkenyl sulphones are preferred Michael Reagents for use in the biological assays of this invention. compounds such as N-ethylmaleimide also react rapidly with proteins by Michael addition and are reasonably stable under the conditions used for labelling proteins, although alkaline hydrolysis is observed when these reagents are polymer bound. Thus maleimide compounds are also preferred Michael Reagents for use in the biological assays of this invention. In most circumstances nitrile reagents are also preferred reagents although a nitrile reagent will tend to react more slowly than corresponding sulphones. Similarly acrylamides react still more slowly. These preferences do not mean that the other Michael reagents available are unsuitable for this invention, but for most purposes rapid reaction of the reagents is preferred. Under appropriate conditions almost any of the Michael reagents could be used in the methods of this invention.

A preferred class of lysine-selective reagents for use in this invention comprise hindered alkenyl sulphones as the lysine selective reactive groups. Combinations of these reagents under appropriate mild conditions can allow a high degree of discrimination between alpha-amino groups and lysine epsilon-amino groups in amine-labelling reactions. Vinyl sulphones are known to react readily with primary amines giving a di-alkylated product. The inventors have shown that these reagents will react more rapidly with epsilon-amino groups at high pHs (>9.0) than with alpha-amino groups but the discrimination of these unhindered sulphones is poor. More hindered alkenyl sulphones such as propenyl sulphones and butenyl sulphones show a greatly enhanced discrimination in favour of epsilon amino groups when compared with the vinyl sulphones. In addition, these hindered reagents produce the mono-alkylated product almost exclusively. Moreover, lysine epsilon-amino groups that have been mono-alkylated with some of the more hindered sulphones are resistant to further reaction with other amine reactive reagents.

This discrimination by hindered sulphones means that epsilon-amino groups can be selectively labelled in preference to alpha-amino groups under mild aqueous conditions with convenient, stable, water-soluble reagents. If a lysine selective capture reagent is required the hindered alkenyl sulphone functional groups of this invention can be linked to a solid support. Alternatively an affinity capture reagent can be generated by linking the hindered alkenyl sulphone functional groups of this invention to biotin or digoxigenin, for example. As a further alternative the hindered alkenyl sulphone functionalities may be covalently linked to a second reactive functionality that is reactive with an appropriately derivitised solid phase support. Boronic acid is known to selectively react with vicinal cis-diols and chemically similar ligands, such as salicylhydroxamic acid. Reagents comprising boronic acid have been developed for protein capture onto solid supports derivitised with salicylhydroxamic acid (Stolowitz M. L. et al., Bioconjug Chem. 12 (2): 229–239, "Phenylboronic Acid-Salicylhydroxamic Acid Bioconjugates. 1. A Novel Boronic Acid Complex for Protein; Wiley J. P. et al., Bioconjug. Chem. 12 (2): Acid-Salicylhydroxamic Acid Bioconjugates. 2. Polyvalent Immobilization of Protein Ligands for Affinity Chromatography." 2001, Prolinx, Inc, Washington State, USA). It is anticipated that it should be relatively simple to link a phenylboronic acid functionality to a hindered alkenyl sulphone functionality to generate capture reagents that can be captured by selective chemical reactions. The use of this sort of chemistry would not be directly compatible with proteins bearing vicinal cis-diol-containing sugars, however these sorts of sugars could be blocked with phenylboronic acid or related reagents prior to reaction with boronic acid derivitised lysine selective reagents. Solution phase capture reagents, that may be captured onto solid supports, are advantageous as the lysine reaction may take place in the solution phase, with a large excess of reagent to drive the reaction to completion quickly.

Numerous methods of synthesising hindered alkenyl sulphones are known in the art. For general reviews of synthetic methods that have been used for the synthesis of alpha-, beta-unsaturated sulphones see Simpkins N., Tetrahedron 46: chemistry of vinyl sulphones", 1990; and Fuchs P. L. and Braish T. F., Chem Rev. 86: 903–917, "Multiply Convergent Synthesis via Conjugate-Addition Reactions to Cycloalkenyl Sulfones", 1986.

Preferred hindered alkenyl sulphone compounds of this invention have the formula:

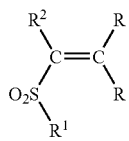

Where $R^1$ may be any alkyl or aromatic group but is preferably an electron withdrawing group and more preferably a cyclic or heterocylic aromatic ring or fused ring. Preferably the ring structure is electron withdrawing. More specifically $R^1$ is preferably a small ring or fused ring such as a phenyl, pyridyl, naphthyl or quinolyl ring structure. Preferred ring structures are substituted with appropriate electron withdrawing groups such as halogens like fluorine or nitro groups. Preferred ring structures promote water solubility, such as pyridyl and naphthyl rings. $R^1$ may additionally comprise a linker to an affinity capture functionality, such as biotin, or a linker to a solid phase support.

In the formula above $R^2$ is either a hydrogen atom or it may comprise an electron-withdrawing group and/or a linker to an affinity capture functionality or a linker to a solid phase support.

To be a 'hindered' Michael reagent according to this invention, at least one of the R groups is not hydrogen and is considered to be a sterically hindering group. At least one R group may comprise an alkyl or aromatic group such as a methyl or phenyl group. More preferably at least one of the R groups is electron-withdrawing and may comprise a halogen atom or a halogenated alkyl group, such as fluoromethyl, difluoromethyl or trifluoromethyl group or a phenyl ring with electron withdrawing substituents such as halogen or nitro groups. In addition, one R-group may comprise a linker to an affinity capture functionality, such as biotin, or a linker to a solid phase support. Conversely to be an 'unhindered' Michael reagent in the context of this invention, both R groups would be hydrogen.

One and preferably, only one of the R—, $R^2$-groups comprises a linker to an affinity capture functionality, such as biotin, or a linker to a solid phase support.

Various entry-points into the synthesis of alkenyl sulphones may be contemplated to produce compounds that are appropriately substituted for use with this invention. Aldol condensation-type reactions can be used. Methyl phenyl sulphone can be reacted with a variety of ketones and aldehydes to give hindered alkenyl sulphones (see FIG. 1 and the reviews above). Appropriate ketones include acetone and hexafluoroacetone. Aldehydes include fluorobenzaldehyde, difluorobenzaldehyde, trifluoromethylbenzaldehyde and nitrobenzaldehyde. 4-(Methylsulfonyl)benzoic acid provides a starting point for the synthesis of a hindered sulphone that can be linked to a solid support or to an affinity capture reagent through the benzoic acid. polystyrene is available from various sources including Sigma-Aldrich, Carbodiimide coupling of the functionalised benzoic acid to generate an amide linkage to the solid support would be sufficient generate a solid support derivitised with the appropriate alkenyl sulphone. Various forms of amino-functionalised biotin are available from Pierce Chemical Company, USA, which would allow a biotin compound derivitised with a variety of alkenyl sulphones to be synthesised.

Synthetic routes for the production of phenyl-1-propenyl, pyridine-1-propenyl, isobutenyl and pyridine-1-isobutenyl sulphones are described in the examples towards the end of this document. A synthetic route for the production of phenylsulphonylpropene is disclosed by Tsuge H. et al. in J. Chem. Soc. Perkin Trans. 1: 2761–2766, 1995. This reagent is also available from Aldrich (SigmaAldrich, Dorset, UK).

A second preferred class of reagents for use in this invention are maleimide compounds. Combinations of these reagents under appropriate mild conditions can allow a high degree of discrimination between alpha-amino groups and lysine epsilon-amino groups in amine-labelling reactions. compounds are known to react readily with primary amines giving a product (see for example: Sharpless N. E. & Flavin M., Biochemistry 5 (9): 2963–2971, "The reactions of amines and amino acids with maleimides. Structure of the reaction products deduced from infrared and nuclear magnetic resonance spectroscopy." 1966; Papini A. & Rudolph S. & G. & J. & Gohring W. & Moroder L., Int J Pept Protein Res 39 (4): 348–355, "Alkylation of histidine with maleimido-compounds." 1992; Khan M. N., J Pharm Sci 73 (12): and mechanism of the alkaline hydrolysis of maleimide." 1984). The inventors have shown that a solid support derivitised with maleimide Fluka) will react more rapidly with epsilon-amino groups under basic conditions than with alpha-amino groups. This reagent is not stable in aqueous conditions, however, and reactions of peptides with this support should be carried out in anhydrous aprotic organic solvents. The use of organic solvents is acceptable for highly hydrophobic proteins, such as proteins embedded in cell membranes and as such is useful for the analysis of this class of proteins.

Some of the less hindered Michael reagents, such as N-ethylmaleimide (NEM) and the propenyl sulphones will react quite readily with the alpha-amino group of proline. This will not be a problem in most aspects of this invention as proline is not common and most endoproteases do not cleave at proline linkages anyway. The preferred embodiment of this invention relies on cleavage of proteins and polypeptides by Lys-C type enzymes. Most of the known enzymes of this class will not cleave at Lysine-Proline linkages, so the presence of a free proline alpha-amino will not present a problem. Solid-support bound maleimide also discriminates effectively against proline. It is worth noting that maleimide shows only moderate discrimination for epsilon amino groups over alpha amino groups when used as a solution phase reagent, but the discrimination of the immobilised reagent is greatly improved. Other reagents, which show only moderate discrimination in the solution phase may show improved discrimination when immobilised on a solid phase support.

Further aspects of this invention provide a method of determining the 'expression profile' of a mixture of polypeptides, i. a method to identify and preferably also to quantify each polypeptide in the mixture, and also methods of comparing polypeptides in two or more mixtures (e.g. from two or more separate samples). These methods involve determining the expression profile of one or more polypeptides in the mixture according to the first embodiment of the invention. Different labels may be employed for each sample in the mixture. The labels can be resolved, so that each expression profile, or each individual polypeptide being compared, will be relatable to a specific sample. Preferred mass labels for use with this invention are disclosed in which discloses organic molecule mass markers that are analysed by selected reaction monitoring. This application discloses two component mass markers connected by a collision cleavable group. Sets of tags are synthesised where the sum of the masses of the two components produces markers with the same overall mass. The mass markers may be analysed after cleavage from their analyte or may be detected while attached to the analyte. In this invention the mass markers are detected while attached to the peptide that they are identifying. Selection of the mass of the mass marker with its associated peptide by the first mass analyser of a tandem instrument allows the marked peptides to be abstracted from the background. Collision of the markers in the second stage of the instrument separates the two components of the tag from each other. Only one of these components is detected in the third mass analyser. This allows confirmation that the peak selected in the first analyser is a mass marked peptide. The whole process greatly enhances the signal to noise ratio of the analysis and improves sensitivity. This mass marker design also compresses the mass range over which an array of mass markers is spread. Moreover, it allows the design of markers, which are chemically identical, have the same mass but which are still resolvable by mass spectrometry. This is essential for analytical techniques such as Liquid Chromatography Mass Spectrometry (LC-MS) where the effect of different markers on the mobility of different samples of peptides must be minimised so that corresponding peptides from each sample elute together into the mass spectrometer, allowing the ratios of the corresponding peptides to be determined. These markers are thus most preferred for the purposes of this invention because of the use of high selectivity detection and the closely related structures of these markers. Other markers may also be applicable, though.

In various embodiments of this invention there is an optional, but preferred first step, which involves reducing cysteine disulphide bridges and capping of free thiols. The alkenyl sulphone reagents of this invention are reactive with free thiols. To prevent interference in the methods of this invention by free thiols, and to avoid problems associated with disulphide bridges in polypeptides, it is preferred that the disulphide bridges are reduced to free thiols and that the thiol moieties are capped prior to application of the methods of this invention. Since thiols are very much more reactive than the other side-chains in a protein this step can be achieved highly selectively.

Various reducing agents have been used for disulphide bond reduction. The choice of reagent may be determined on the basis of cost, or efficiency of reaction and compatibility with the reagents used for capping the thiols (for a review on these reagents and their use see Jocelyn P. C., Methods Enzymol. 143: 246–256, "Chemical reduction of disulfides." (1987).

Typical capping reagents include iodoacetamide, vinylpyridine, 4-nitrostyrene, methyl vinyl sulphone or ethyl vinyl sulphone. (see for example Krull L. H. & Gibbs D. E. & Friedman M., Anal Biochem 40: 80–85, "2-Vinylquinoline, a reagent to determine protein groups; Masri M. S. & Windle J. J. & Friedman M., Biochem Biophys Res Commun 47 (6): 1408–1413, "p-Nitrostyrene: new alkylating agent for sulfhydryl groups in reduced soluble proteins and keratins." 1972; Friedman M. & J. C. & Wagner J. R., Anal Biochem 106: 27–34, "Estimation of the disulfide content of trypsin inhibitors as Typical reducing agents include mercaptoethanol, dithiothreitol (DTT), sodium borohydride and phosphines such as tributylphosphine (see Ruegg U. T. & Rudinger J., Methods Enzymol 47: 111–116, "Reductive cleavage of cystine disulfides with tributylphosphine.", 1977) and tris(carboxyethyl) phosphine (Burns J. A. et Org Chem 56: reduction of disulfide by Tris(2-carboxyethyl) phosphine.", 1991). Mercaptoethanol and DTT may be less preferred for use with thiol reactive capping reagents as these compounds contain thiols themselves. Phosphine based reducing reagents are compatible with vinyl sulphone reagents (Masri M. S. & Friedman M., J. Protein Chem. 7: 49–54, 'Protein reactions with methyl and ethyl vinyl sulfones.' 1988). It is worth noting that the reduction and thiol blocking may take place simultaneously with the epsilon-amino labelling step of the second aspect of this invention.

In various embodiments of this invention a sequence specific cleavage reagent is required. Preferred cleavage reagents for use with this invention are enzymatic reagents. Trypsin is a preferred enzyme for the cleavage of polypeptides. This reagent is the enzyme most widely used for conventional peptide mass fingerprinting. Trypsin is preferred for a number of reasons. It is a highly robust enzyme, tolerating moderate amounts of detergents and denaturants, while still retaining the ability to cleave polypeptides. In addition, if cleavage of the polypeptides proceeds to completion, then each digest peptide has a basic residue at each terminus of the peptide, except, for the C-terminal peptides and some blocked N-terminal peptides. The presence of basic residues promotes protonation of the peptides. Various enzymes that cut a polypeptide or peptide at the amide bond C-terminal to a lysine residue are commercially available, e.g. Endoproteinase Lys-C from Lysobacter enzymogenes (Formerly available from Mannheim now from Roche Biochemicals). These enzymes are generically referred to as Lys-C and are also preferred enzymes for use with this invention. Similarly, enzymes that cut a polypeptide or peptide at the amide bond C-terminal to an arginine residue are commercially available and are generically referred to as Arg-C enzymes. These are also preferred enzymes for use with this invention. Chemical cleavage may also be applicable with this method. A reagent such as cyanogen bromide which cleaves at methionine residues would be appropriate. Chemical cleavage may be advantageous because protease inhibitors may be used during the isolation of the sample of polypeptides from its biological source. The use of protease inhibitors will reduce non-specific degradation of the sample by endogenous proteases. Chemical reagents can also be readily by addition of appropriate quenching reagents.

In certain embodiments of this invention the mass markers comprise an affinity capture ligand. Affinity capture ligands are ligands, which have highly specific binding partners.

These binding partners allow molecules tagged with the ligand to be selectively captured by the binding partner. Preferably a solid support is derivitised with the binding partner so that affinity ligand tagged molecules can be selectively captured onto the solid phase support. A preferred affinity capture ligand is biotin, which can be introduced into the peptide mass tags of this invention by standard methods known in the art. In particular a lysine residue may be incorporated after amino acid 2 through which an amine-reactive biotin can be linked to the peptide mass tags (see for example Geahlen R. L. et al., Anal Biochem 202: 68–67, "A general method for preparation of peptides biotinylated at the carboxy terminus." 1992; Sawutz D. G. et al., Peptides 12 (5): 1019–1012, "Synthesis and molecular characterization of a biotinylated analog of [Lys]; Natarajan S. et al., Int J Pept Protein Res 40 (6): biotinylation. A novel approach and its application to endothelin-1 analogs and 1992). Iminobiotin is also applicable. A variety of avidin counter-ligands for biotin are available, which include monomeric and tetrameric avidin and streptavidin, all of which are available on a number of solid supports.

Other affinity capture ligands include digoxigenin, fluorescein, nitrophenyl moieties and a number of peptide epitopes, such as the epitope, for which selective monoclonal antibodies exist as counter-ligands. Metal ion binding ligands such as hexahistidine, which readily binds ions, are also applicable. Chromatographic resins, which present iminodiacetic acid chelated ions are commercially available, for example. These immobilised nickel columns may be used to capture tagged peptide, which comprise histidine. As a further alternative, an affinity capture functionality may be selectively reactive with an appropriately derivitised solid phase support. Boronic acid, for example, is known to selectively react with vicinal cis-diols and chemically similar ligands, such as salicylhydroxamic acid. Reagents comprising boronic acid have been developed for protein capture onto solid supports derivitised with salicylhydroxamic acid (Stolowitz M. L. et al., Bioconjug Chem 12 (2): 229–239, "Phenylboronic Acid—Salicylhydroxamic Acid Bioconjugates. 1. A Novel Boronic Acid Complex for Protein Immobilization." 2001; Wiley J. P. et al., Bioconjug Chem 12 (2): 240–50, "Phenylboronic Acid Bioconjugates. 2. Polyvalent Immobilization of Protein Ligands for Affinity Chromatography." 2001, Prolinx, Inc, Washington State, USA). It is anticipated that it should be relatively simple to link a phenylboronic acid functionality to the tags of this invention to generate capture reagents that can be captured by selective chemical reactions. The use of this sort of chemistry would not be directly compatible with biomolecules bearing vicinal cis-diol-containing sugars, however these sorts of sugars could be blocked with phenylboronic acid or related reagents prior to reaction with boronic acid derivitised tag reagents.

The methods of this invention can be used to profile populations of proteins generated in numerous ways. It may be possible to analyse raw protein extracts from organisms such as yeast directly using the methods of this invention. Organisms with larger proteomes may require fractionation of the raw protein extracts from their tissues. Various fractionation exist to sub-sort proteins on the basis of certain features. A population of proteins extracted from a mammalian tissue, for example, is going to contain a significant number of distinct protein species. It is thought there are of the order of 10,000 transcripts, which may comprise alternatively spliced products from numerous genes, expressed in the average human cell (Iyer V. R. et Science 283 (5398) 83–87, "The transcriptional program in the response of human fibroblasts to serum." 1999), and experiments with 2-D gels have shown that similar numbers of proteins spots are found in gels of proteins extracted from a particular tissue (Klose J., Kobalz U., Electrophoresis 16 (6) 1034–59, "Two-dimensional electrophoresis of proteins: an updated protocol and implications for a functional analysis of the genome." 1995). It may be desirable to fractionate complex samples of proteins, such as those that would be isolated from human tissue, prior to application of the methods of this invention to simplify analysis or to provide additional information, such as identifying proteins with modifications.

Fractionation steps can be used to reduce the complexity of a population of proteins by resolving a protein population into a number of discrete subsets, preferably subsets of a uniform size are desirable. This is most readily achieved by separation on the basis of global properties of proteins, that vary over a broad and continuous range, such as size and surface charge. These are the properties used most effectively in 2-D gel electrophoresis. Such separations can be achieved more rapidly than gel electrophoresis using liquid chromatographic techniques. By following one liquid chromatography separation by another, a population of proteins can be resolved to an arbitrary degree, although a large number of sequential chromatographic separation steps could result in sample loss or other artefacts due to non-specific adhesion of proteins or peptides to different chromatographic matrices.

Cell Fractionation

Proteins are compartmentalised within their cells. Various techniques are known in the art to fractionate proteins on the basis of their cellular compartments. Fractionation protocols involve various cell lysis techniques such as sonication, detergents or mechanical cell lysis that can be followed by a variety of fractionation techniques, such as centrifugation. Separation into membrane proteins, cytosolic proteins and the major membrane bound compartments, such as the nucleus and mitochondria, is standard practice. Thus certain classes of protein may be effectively ignored or can be specifically analysed. This form of fractionation may be extremely informative if a particular protein is found in a number of locations since its location is likely to reveal information about its function.

Fractionation of Proteins

Since proteins are highly heterogeneous molecules numerous techniques for separation of proteins are available. It is possible to separate proteins on the basis of size, hydrophobicity, surface charge by affinity to particular ligands. Separation is effected by an assortment of solid phase matrices derivatised with various functionalities that adhere to and hence slow down the flow of proteins through the column on the basis of specific properties. Matrices derivitised with hydrophobic moieties can be used to separate proteins based on their hydrophobicity, while charged resins can be used to separate proteins on the basis of their charge. In a typical chromatographic separation, analyte molecules are injected into columns packed with these a derivitised resin in a loading buffer or solvent that favours adhesion to the solid phase matrix. This is followed by washing the column with steadily increasing quantities of a second buffer or solvent favouring elution. In this way the proteins with the weakest interactions with a given matrix elute first.

Fractionation by Affinity

A population of proteins can be fractionated by affinity methods. This sort of fractionation method relies on specific interactions between proteins, or classes of proteins, with specific ligands.

Many proteins, for example, exist as complexes with other proteins and analysis of such complexes is often difficult. A cloned protein that is a putative member of a complex can be used to generate an affinity column with the cloned protein acting as an affinity ligand to capture other proteins that normally bind to it. This invention is eminently suited to the analysis of such captured protein complexes.

Isolation of Post-translationally Modified Proteins

A large number of affinity ligands are available commercially for specific applications such as the isolation of proteins with modifications. A number of tagging procedures are also known by which affinity tags such as biotin can be introduced into proteins that have specific post-translational modifications allowing such proteins to be captured using biotin-avidin affinity chromatography.

Isolation of Carbohydrate Modified Proteins

Carbohydrates are often present as a post-translational modification of proteins. Various affinity chromatography techniques for the isolation of these sorts of proteins are known (For a review see Gerard C., Methods Enzymol. of glycoproteins." 1990). A variety of natural protein receptors for carbohydrates are known. The members of this class of receptors, known as lectins, are highly selective for particular carbohydrate functionalities. Affinity columns derivitised with specific lectins can be used to isolate proteins with particular carbohydrate modifications, whilst affinity columns comprising a variety of different lectins could be used to isolate populations of proteins with a variety of different carbohydrate modifications. Many carbohydrates have vicinal-diol groups present, i.e. hydroxyl groups present on adjacent carbon atoms. Diol containing carbohydrates that contain vicinal diols in a 1,2-cis-diol configuration will react with boronic acid derivatives to form cyclic esters. This reaction is favoured at basic pH but is easily reversed at acid pH. Resin immobilised derivatives of phenyl boronic acid have been used as ligands for affinity capture of proteins with cis-diol containing carbohydrates. Vicinal-diols, in sialic acids for example, can also be converted into carbonyl groups by oxidative cleavage with periodate. Enzymatic oxidation of sugars containing terminal galactose or galactosamine with galactose oxidase can also convert hydroxyl groups in these sugars to carbonyl groups. Complex carbohydrates can also be treated with carbohydrate cleavage enzymes, such as which selectively remove specific sugar modifications leaving behind sugars, which can be oxidised. These carbonyl groups can be tagged allowing proteins bearing such modifications to be detected or isolated. hydrazide (Pierce & Warriner Ltd, Chester, UK) will react with carbonyl groups in carbonyl-containing carbohydrate species (E. A. Bayer et al., Anal. Biochem. 170,271–281, "Biocytin hydrazide—a selective label for sialic acids, galactose, and other sugars in glycoconjugates using avidin biotin technology", Alternatively a carbonyl group can be tagged with an amine modified biotin, such as PEO-Biotin (Pierce & Warriner Ltd, Chester, using reductive alkylation (Means G. E., Methods Enzymol 47,469–478, "Reductive alkylation of amino groups." 1977; I., Methods Enzymol 276: 171–179, "Reductive alkylation of lysine residues to alter crystallization properties of proteins." 1997). Proteins bearing vicinal-diol containing carbohydrate modifications in a complex mixture can thus be biotinylated. hence carbohydrate modified, proteins may then be isolated using an avidinated solid support.

Peptides may then be isolated and analysed from the captured carbohydrate bearing proteins isolated using the above methods.

Isolation of Phosphorylated Proteins

Phosphorylation is a ubiquitous reversible post-translational modification that appears in the majority of signalling pathways of almost all organisms. It is an important area of research and tools which allow the analysis of the dynamics of phosphorylation are essential to a full understanding of how cells responds to stimuli, which includes the responses of cells to drugs.

A number of research groups have reported on the production of antibodies, which bind to phosphotyrosine residues in a wide variety of proteins. (see for example A. R. Frackelton et Methods Enzymol. 201, 79–92, "Generation of monoclonal antibodies against phosphotyrosine and their use for affinity purification of phosphotyrosine-containing proteins.", 1991 and other articles in this issue of Methods Enzymol.). This means that a significant proportion of proteins that have been post-translationally modified by tyrosine phosphorylation may be isolated by affinity chromatography using these antibodies as the affinity column ligand.

These phosphotyrosine binding antibodies can be used in the context of this invention to isolate peptides from proteins containing phosphotyrosine residues. The tyrosine-phosphorylated proteins in a complex mixture may be isolated using anti-phosphotyrosine antibody affinity columns. The peptides from the fractionated mixture of phosphoproteins may then be isolated and analysed according to the methods of this invention.

Techniques for the analysis of phosphoserine and phosphothreonine containing peptides are also known. One class of such methods is based a well known reaction for beta-elimination of phosphates. This reaction results in phosphoserine and phosphothreonine forming dehydroalanine and both of which are Michael acceptors and will react with thiols. This has been used to introduce hydrophobic groups for affinity chromatography (See for example Holmes C. F., FEBS Lett 215 (1) 21–24, "A new method for the selective isolation of phosphoserine-containing peptides." 1987). Dithiol linkers have also been used to introduce fluorescein and biotin into phosphoserine and phosphothreonine containing peptides (Fadden P, Haystead T A, Anal Biochem 225 (1) 81–8, "Quantitative and selective fluorophore labelling of phosphoserine on peptides and proteins: characterization at the attomole level by capillary electrophoresis and laser-induced fluorescence." 1995 Nature Biotech 19,379–382, "Enrichment analysis of phosphorylated proteins as a tool for probing the phosphoproteome", 2001). The use of biotin for affinity enrichment of proteins phosphorylated at serine and threonine could be used with the methods of this invention so that only the terminal peptides need to be analysed. Similarly anti-fluorescein antibodies are known which would allow fluorescein tagged peptides to be selectively isolated with affinity chromatography. This could be followed by peptide isolation and analysis according to the methods of this invention.

A chemical procedure for the isolation of phosphoproteins onto solid phase supports has also been published (Zhou H et Nature Biotech 19,375–378, "A systematic approach to the analysis of protein phosphorylation", 2001). This procedure relies on the fact that hydrolyse easily under acid conditions. The procedure involves capping all free amines in a mixture of proteins, followed by blocking all free phosphates and carboxyl groups by coupling the phosphates and carboxyls with a capping group containing an amine functionality to form the corresponding phosphoramidates and amides. The blocked proteins are then treated with acid to unblock the phosphates. The peptides are then reacted with a second amine reagent carrying a protected thiol. This step blocks the phosphates again. The protected thiol was deprotected and used to capture the phosphopeptides selectively onto a thiol reactive resin. These peptides could then be released by acid hydrolysis, after thorough washing of the resin. This procedure is claimed to be applicable to all phosphate groups but phosphotyrosine is acid labile and so the method is unlikely to applicable to phosphotyrosine.

Immobilised Metal Affinity Chromatography (IMAC) represents a further technique for the isolation of phosphoproteins and Phosphates adhere to resins comprising trivalent metal ions particularly to Gallium ions (Posewitch, M. C. and Tempst, P., Anal. Chem., 71: Gallium (III) Affinity Chromatography of Phosphopeptides", 1999). This technique is advantageous as it can isolate both serine/threonine phosphorylated and tyrosine phosphorylated peptides and proteins simultaneously.

IMAC can therefore also be used in the context of this invention for the analysis of samples of phosphorylated proteins. In an alternative embodiment of the second aspect of this invention, a sample of phosphorylated proteins may be analysed by isolating phosphorylated proteins followed by analysis of the peptides of the phosphoproteins. A protocol for the analysis of a sample of proteins, which contains phosphorylated proteins, would comprise the steps of:

1. passing the protein sample through an affinity column comprising immobilised metal ions to isolate only phosphorylated proteins, 2. isolating and analysing the peptides from the captured phosphorylated proteins using the methods of this invention, Other Post-translational Modifications of Proteins Proteins that have been modified by lipoylation and other post-translational modifications may also be isolated or enriched by chromatographic techniques (Gibson J. C., Rubinstein A., Ginsberg H. N. & Brown W. V., Methods Enzymol 129,186–198, "Isolation of apolipoprotein E-containing lipoproteins by immunoaffinity chromatography."[1] 1986; Tadey T. & Purdy W. C. J B Biomed. Appl. 671 (1–2), 237–253, "Chromatographic techniques for the isolation and purification of or affinity ligand based techniques such as (Hershko A., Eytan Ciechanover A. & Haas A. L., J. Biol. Chem. 257, (23) analysis of the turnover of ubiquitin-protein conjugates in intact cells. Relationship to the breakdown of abnormal proteins." 1982). Populations of proteins with these modifications can all be analysed by the methods of this invention.

In preferred embodiments of this invention the lysine-selective tags comprise sensitivity enhancing groups. Various functionalities can be used as sensitivity enhancing groups.

The choice of functionality is largely determined by the mass spectrometric analysis technique to be used. The guanidino group and the tertiary amino group are both useful Sensitivity Enhancing Groups for electrospray mass spectrometry (Francesco L. Branca, Stephen G. Oliver and Simon J. Gaskell, Rapid Commun. in Mass Spec., 14, 2070–2073, "Improved matrix-assisted laser desorption/ionization mass spectrometric analysis of hydrolysates of proteins following guanidination of lysine-containing peptides." 2000).

Various other methods for derivatising peptides have been also been developed. These include the use of quaternary ammonium derivatives, quaternary phosphonium derivatives and pyridyl derivatives for positive ion mass spectrometry. Halogenated compounds, particularly halogenated aromatic compounds are well known electrophores, i.e. they pick up thermal electrons very easily. A variety of derivatisation reagents based on fluorinated aromatic compounds (Bian N. et al., Rapid Commun Mass Spectrom 11 (16): 1781–1784, "Detection via laser desorption and mass spectrometry of multiplex have been developed for electron capture detection, which is a highly sensitive ionisation and detection process that can be used with negative ion mass spectrometry (Abdel-Baky S. & Giese R. W., Anal. Chem. 63 (24): 2986–2989, "Gas capture negative-ion mass spectrometry at the zeptomole level." A fluorinated aromatic group could also be used as a sensitivity enhancing group. Aromatic sulphonic acids have also been used for improving sensitivity in negative ion mass spectrometry.

Each type of sensitivity enhancing group has different benefits, which depend on the method of ionisation used and on the methods of mass analysis used. The mechanism by which sensitivity is enhanced may also be different for each type of group. Some derivitisation methods increase basicity and thus promote protonation and charge localisation, while other methods increase surface activity of the tagged peptides, which improves sensitivity in surface desorption techniques like Matrix Assisted Laser Desorption Ionisation (MALDI) and Fast Atom Bombardment Negative ion mass spectrometry is often more sensitive because there is less background noise. Charge derivitisation can also change the fragmentation products of derivatised peptides, when collision induced dissociation is used. In particular some derivatisation techniques simplify fragmentation patterns, which is highly advantageous, if peptides are to be analysed by techniques such as collision induced dissociation. The choice of Sensitivity Enhancing Group is determined by the mass spectrometric techniques that will be employed (for a review see Roth et Mass Spectrometry Reviews 17: 255–274, "Charge derivatization of peptides for analysis by mass spectrometry", For the purposes of this invention all of the known sensitivity enhancing groups could be used with the lysine-selective tags of this invention.

In preferred embodiments of this invention, the lysine-selective alkenylsulphone reagents comprise a non-fluorescent dye. Preferably, the tags comprise a dye that has a high extinction coefficient for a particular frequency of light and which dissipates absorbed energy through vibrational modes. Some examples of such dyes are used as matrices for MALDI-TOF mass spectrometry where excitation of the dyes by laser light leads to rapid sublimation of the dyes. This sublimation process also vaporises any co-crystallised material. Cinnamic acid derivatives are preferred dyes that are widely used in MALDI TOF (Beavis R C, Chait B T, Rapid Commun Mass Spectrom 3 (12): 432–435, "Cinnamic acid derivatives as matrices for ultraviolet laser desorption mass spectrometry of proteins." 1989). The inventors have found, in that covalently linking derivatives of cinnamic acid, and other dyes?, to peptides greatly increases the yield of ions from the attached peptides. Therefore, alkenyl sulphone reagents, that comprise cinnamic acid derivatives are preferred tags for use with this invention.

In some embodiments of this invention, the alpha-amino groups of peptides from digested polypeptides may be tagged with sensitivity enhancing groups. esters of cinnamic acid derivatives, such as acid, may be excellent tags for this purpose.

Determination of Peptide Mass Fingerprints

Some of the less hindered Michael reagents, such as (NEM) and the propenyl sulphones will react quite readily with proline. This will not be a problem in most aspects of this invention as proline is not common and most endoproteases do not cleave at proline linkages anyway. Some aspects of this invention rely on cleavage of proteins and polypeptides by Lys-C type enzymes. Most of the known enzymes of this class will not cleave at Lysine-Proline linkages, so the presence of a free proline alpha-amino is unlikely unless it occurs at the N-terminus of a protein. Similarly trypsin will not cleave at lysine-proline or arginine-proline linkages and is useable in the first and second aspects of this invention to avoid the production of free proline alpha-amino groups. An N-terminal proline will only be a problem for this invention where the proline is unblocked. Improved proline lysine discrimination is, however, found in the more-hindered alkenyl sulphones such as the isobutenyl sulphones, the trifluoropropenyl sulphones and the hexafluoroisobutenyl sulphones, so these reagents should be used if discrimination against proline is required.

In one embodiment of this invention, which describes a general method to produce peptide mass fingerprints of lysine labelled polypeptides, the discrimination of the hindered sulphones is used to specifically label epsilon-amino groups. This reaction follows cleavage of the polypeptide or mixture of polypeptides with a sequence specific cleavage reagent, which can be enzymatic such as trypsin or can be chemical such as bromide. The cleavage of the mixture of polypeptides with the sequence specific cleavage reagent will expose alpha-amino groups in all the resulting cleavage peptides. The lysine-selective tags of this invention are reacted with the digested peptides and the tags will selectively react with epsilon-amino groups in preference to any alpha-amino groups that are available. These labelled peptides are then analysed by mass spectrometry to determine a peptide mass fingerprint from the labelled peptides.

In certain embodiments of this embodiment of the invention, the lysine-selective tags may comprise an affinity tag. This allows peptides that have been labelled on their lysine residues to be selectively isolated from peptides that do not contain lysine and which may contaminate the mass spectrum generated from the labelled digest. In one preferred embodiment, the polypeptide or polypeptides to be analysed are digest with trypsin as shown in FIG. 2. Trypsin cleaves at both arginine and lysine generating peptides that terminate at both arginine and lysine. If the digestion is allowed to proceed to completion, then cleavage will have taken place at substantially all of the available lysine and arginine residues and each of the digest peptides will contain only one lysine or arginine residue except for C-terminal peptides, which will contain neither lysine nor arginine. This means that labelling the digest peptides with a lysine-selective tag will introduce one and only one tag into those peptides that contain lysine. If, as shown in FIG. 4, the lysine-selective tag comprises an affinity tag, like biotin, then the lysine containing peptides that are labelled can be isolated by affinity chromatography, using an avidinated solid support if the affinity tag is biotin. This results in a reduced subset of the digest peptides that can then be analysed by MALDI TOF mass spectrometry to determine a peptide mass fingerprint for the chosen polypeptide or polypeptides. The use of an affinity tag is highly advantageous as isolation of the peptides allows the lysine containing peptides to be separated from arginine containing peptides. This reduces the potential for competition during ionisation, which favours ionisation of arginine containing peptides. Furthermore, the labelled peptides can be isolated from lysine-containing peptides that have not reacted with the tags and from terminal peptides that do not contain lysine or arginine. In addition, capturing the peptides onto a solid support allows the isolated peptides to be conditioned for mass spectrometry. This means that any detergents, denaturants and polymeric buffering agents that may have been used during the isolation of the polypeptide, during digestion of the polypeptide or during labelling of the polypeptide can be washed away. Non-volatile buffer components such as metal ions from the peptide buffers can also be exchanged for ammonium ions by washing the peptides on the support with appropriate ammonium ion containing buffers to ensure that metal ion adducts of the peptides do not contaminate the mass spectrum of the peptide digest. If biotin and avidin are used as the affinity tag and counter-ligand respectively then the sequence specific cleavage reagent used to digest the polypeptide or polypeptides must be inactivated before the labelled peptides are isolated onto an avidinated support. If the cleavage agent is still active it will digest the avidinated support releasing the captured peptides. The labelling of lysine functionalities may inactivate the cleavage reagent if it is enzymatic but it is also preferable to add an inhibitor of the enzyme after digestion is complete. The lysine-selective tag comprising the affinity tag may additionally comprise a sensitivity enhancing group to improve the peptide mass fingerprint. Alternatively, the captured peptides, which in most cases will have exposed alpha-amino groups, can be reacted with an amino-reactive reagent thereby linking a sensitivity enhancing group to the peptide. Peptides derived from the N-terminus of a polypeptide are sometimes blocked and so these blocked peptides would not be labelled if an alpha-amino labelling strategy is used.

In other embodiments of this invention, lysine selective tags that comprise affinity tags can be used in conjunction with sequence specific cleavage agents other than trypsin.

FIG. 3 shows the use of Lys-C. Lys-C, however, is sometimes less preferred than trypsin as the peptides that result from the digestion of a polypeptide with Lys-C may contain one or more arginine residues which may compete for ionisation with peptides that do not contain arginine and may also promote the formation of ions that have been multiply protonated. However, Lys-C is advantageous as it is possible to ensure that each peptide receives only one tag per peptide, assuming the digestion goes to completion and bearing in mind that most C-terminal peptides will not have a lysine after cleavage of a polypeptide with Lys-C. Trypsin will generate peptides that have either a C-terminal lysine or a C-terminal arginine. Arginin containing peptides tend to be detected more readily by mass spectrometry, because of the very basic guanidino-functionality of arginine (Krause E. & Wenschuh & Jungblut P. R., Anal Chem. 71 (19): 4160–4165, "The dominance of arginine-containing peptides in MALDI-derived tryptic mass fingerprints of proteins." 1999). Lysine selective tags can be used to selectively label peptides that do not contain arginine. The tags can be used to introduce a guanidino-functionality, which can help to facilitate the detection of lysine containing peptides (Brancia et al., Electrophoresis: combination of chemical derivitisation and improved tools optimises protein identification for proteomics", 2001).

Expression Profiling and Peptide Mass Fingerprints

This embodiment of the invention provides methods of comparing the expression levels of polypeptides in different samples using peptide mass fingerprinting. To compare the expression profile of two samples it is necessary to determine the identity and relative quantities of each of the component polypeptides in the two samples. This embodiment provides methods to determine both the identity and the relative quantities of each of the component polypeptides in two or more different samples. To achieve this the polypeptides in each sample are labelled with labels that can be resolved by mass spectrometry. The labelled polypeptides are then pooled. The components of the pooled samples are resolved from each other by separating the components using electrophoretic or chromatographic procedures. The separated proteins can then be identified by peptide mass fingerprinting. The use of the labelling procedures described in this invention also allows the relative levels of each component polypeptide to be determined during the mass spectrometric identification of the polypeptides.

Direct quantification of analytes by mass spectrometry is highly unreliable and accurate quantification by mass spectrometry is generally achieved by comparing an analyte with a 'standard' which usually comprises a known quantity of the same material that has an isotopically different mass from the analyte. The standard is usually spiked into the sample just before analysis. The ratio of the analyte to the standard can be used to calculate the quantity of the material. In some situations, the exact quantity is not necessary and the ratio of two isotopes of a substance is sufficient. This is true for protein expression profiling. It is sufficient to be able to determine the ratio of the same polypeptide in different sample to understand how the samples differ from each other. To achieve this the two polypeptides must be isotopically differentiated prior to analysis by mass spectrometry. This can be achieved by labelling the polypeptides in each sample with different isotopes of a tag compound. In the context of this invention, the labelling of polypeptides in different samples takes place prior to the separation of the polypeptides in the samples. This means that the labels must not change the chromatographic behaviour of the labelled proteins. Preferred labels with the necessary properties for use with this invention are disclosed in discloses organic molecule mass markers that are analysed by selected reaction monitoring in a mass spectrometer capable of serial mass analyses, such as an ion trap or triple quadrupole mass spectrometer. discloses mass markers, which have two components connected by a collision cleavable group. Sets of tags are synthesised where the sum of the masses of the two components produces markers with the same overall mass. If each of the components of the mass marker are different isotopes then it is possible to create mass markers that are chemically identical and which have the same mass but have a different mass distribution on either side of the collision cleavable bond. The mass markers may be analysed after cleavage from their analyte or may be detected while attached to the analyte. In the context of the present invention the mass markers, disclosed in are detected while attached to the peptide that they are identifying. Selection of the mass of the mass marker with its associated peptide by the first mass analyser of a tandem instrument allows the marked peptides to be abstracted from the background. If two identical peptides with different tags are present, i.e. peptides from different samples, they will have the same mass in the first stage of analysis and will be selected together. Collision of the marked peptides in the second stage of the instrument separates the two components of the tags from each other. Only one of these components for each tag is detected in the third mass analyser. The ratio of the intensities of the tag fragments from each peptide is a direct measure of the ratio of the peptides in the original sample material. The identification of the tag fragments also provides confirmation that the peak selected in the first analyser is a mass marked peptide. The whole process greatly enhances the signal to noise ratio of the analysis and improves sensitivity. This mass marker design also compresses the mass range over which an array of mass markers is spread. Moreover, it allows the design of markers, which are chemically identical, have the same mass but which are still resolvable by mass spectrometry. This is essential for analytical techniques such as 2-D gel electrophoresis or Liquid Chromatography Mass Spectrometry (LC-MS) where the effect of different markers on the mobility of different samples of peptides must be so that corresponding peptides and polypeptides from each sample move together during fractionation procedures. This is essential to allow the ratios of the corresponding peptides to be determined. These markers are thus most preferred for the purposes of this invention because of the use of high selectivity detection and the closely related structures of these markers. The label compounds disclosed in can be modified so that they will react with polypeptides using the preferred alkenyl sulphone reactive functionalities provided by this invention. Other markers may also be applicable, though.

A set or array of labels, of the form disclosed in PCT/GB01/01122, can be used with the methods of the present invention to increase the of a 2-D gel electrophoresis analysis of the polypeptides in a biological sample. Each of the mass labels alters the mobility of its associated polypeptide in the same way but is still independently detectable. If the tags used comprise a group that can be immobilised on a solid support, such as biotin, then the proteins can be immobilised on an avidinated resin to allow conditioning for mass spectrometric analysis.

In a preferred embodiment of the invention, a method is provided for the analysis of a series of polypeptide containing samples, each sample containing more than one polypeptide, the method comprising the steps 1. Covalently reacting the polypeptides of each of the samples with at least one discretely resolvable mass label, such that the polypeptides of each sample are labelled with one or more mass labels that are different from the labels reacted with the proteins of every other sample.

2. Pooling the mass labelled samples.

3. Optionally separating the pooled samples by gel electrophoresis, iso-electric focusing, liquid chromatography or other appropriate means to generate discrete fractions. These fractions may be bands or spots on a gel or liquid fractions from a chromatographic separation. Fractions from one separation may be separated further using a second separation technique. Similarly further fractions may be fractionated again until the proteins are sufficiently resolved for the subsequent analysis steps.

4. Digesting the polypeptide or polypeptides in each fraction with a sequence specific cleavage reagent 5. Analysing the digests by mass spectrometry, to identify the polypeptides in the fraction and to detect the labels attached to the proteins.

FIG. 6 shows a suitable labelling procedure for use in another embodiment of this invention. In this figure the procedure is shown for a single polypeptide and the separation steps are omitted. In the first step of FIG. 6, the polypeptide is treated with a reducing agent to break disulphide bridges in the molecule followed by capping of the free thiols that result. Free epsilon amino groups are then capped with a hindered alkenyl sulphone tag. If different samples are to be compared then a different tag would be used for each sample. At this stage, labelled samples would be pooled and any fractionation procedures that are necessary would be performed. The final step of FIG. 6 shows digestion of the labelled polypeptide with trypsin, which can now only cleave at arginine residues. This step would take place after fractionation of the labelled polypeptides if a complex mixture is to be analysed.

A further preferred embodiment of the present invention provides a method of identifying a protein in a sample containing more than one protein, the method comprising the steps of:

1. Covalently reacting the proteins of the sample with at least one discretely resolvable mass label from the sets and arrays of this invention.
2. Optionally separating the proteins by gel electrophoresis, iso-electric focusing, liquid chromatography or other appropriate means to generate discrete fractions. These fractions may be bands or spots on a gel or liquid fractions from a chromatographic separation. Fractions from one separation may be separated further using a second separation technique. Similarly further fractions may be fractionated again until the proteins are sufficiently resolved for the subsequent analysis steps.
3. Digesting the proteins in the fraction with a sequence specific cleavage reagent.
4. Optionally reacting the proteins in the sample with an additional mass label.
5. Analysing the digested fractions by liquid chromatography mass spectrometry where the elution time of mass marked peptides from the liquid chromatography column step is determined by detecting the mass labels attached to the peptides. A mass spectrometry analysis is performed, preferably according to an aspect of this invention, to detect the labels attached to the proteins.
6. Analysing the digests by mass spectrometry, to identify the polypeptides in the fraction and to detect the labels attached to the proteins.

In the above preferred embodiments of this aspect of the invention, the step of fractionating the proteins is preferably effected by performing 2-dimensional gel electrophoresis, using iso-electric focusing in the first dimension and SDS PAGE in the second dimension. Typically, the gel is visualised to identify where proteins have migrated to on the gel. Visualisation of the gel is typically performed by staining the gel to reveal protein spots. Various staining procedures and reagents have been developed, although many stains are not compatible with mass spectrometry or require extensive de-staining procedures prior to mass spectrometry. Silver staining is generally regarded as one of the most sensitive staining procedures although it requires de-staining prior to mass spectrometry (Gharahdaghi F et al., Electrophoresis 20 (3): 601–605, "Mass spectrometric identification of proteins from silver-stained polyacrylamide gel: a method for the removal of silver ions to enhance sensitivity." 1999). Novel fluorescent stains that are compatible with mass spectrometry have also been developed. (Lopez M F et al., Electrophoresis 21 (17): 3673–3683, "A comparison of silver stain and SYPRO Ruby Protein Gel Stain with respect to protein detection in two-dimensional gels and identification by peptide mass profiling." 2000). For the purposes of this invention, any of the conventional staining procedures that are compatible with mass spectrometry may be used with the methods of this invention. The proteins in each spot are then identified. There are two approaches to this. In the first approach, the proteins are extracted from the gel. Robotic instrumentation can be used to excise the protein containing spots from the gel. The proteins are then extracted from the excised gel spot. These extracted proteins are then digested and the digest peptides from the polypeptides are analysed by mass spectrometry to determine a peptide mass fingerprint, usually by MALDI TOF mass spectrometry but electrospray mass spectrometry is also quite widely used. Proteins can also be extracted by electroblotting onto a polyvinylidene difluoride membrane after which enzymatic digestion of the proteins can take place on the membrane (Vestling M M, Fenselau C, Biochem Soc Trans 22 (2): difluoride (PVDF): an interface for gel electrophoresis and matrix-assisted laser desorption/ionisation mass spectrometry", 1994). In the second approach the polypeptides are digested in the gel, and the digest peptides are extracted from the gel or from excised gel spots for determination of peptide mass fingerprints by mass spectrometry (Lamer S, Jungblut J Chromatogr B Biomed Sci Appl 752 (2): 311–322, "Matrix-assisted laser desorption-ionisation mass spectrometry peptide mass fingerprinting for proteome analysis: identification efficiency after on-blot or in-gel digestion with and without desalting procedures." 2001).

In step 4, the digested proteins are optionally reacted with an additional mass label of this invention. Most enzymatic digestions and some of the chemical cleavage methods leave free amines on the resultant peptides of the digested fractionated proteins which can be reacted with a mass label. This means that the same label will appear on all peptides and can be detected selectively to maximise the sensitivity of this analysis. This label could comprise a sensitivity enhancing functionality, preferably the tag comprises a cinnamic acid derivative.

Analysis of Peptides by Mass Spectrometry

The essential features of a mass spectrometer are as follows:

Inlet System→Ion Source→Mass Analyser→Ion Detector→Data Capture System

There are preferred inlet systems, ion sources and mass analysers for the purposes of analysing peptides.

Inlet Systems

A variety of mass spectrometry techniques are compatible with separation technologies particularly capillary zone electrophoresis and High Performance Liquid Chromatography (HPLC). The choice of ionisation source is limited to some extent if a separation is required as ionisation techniques such as MALDI and FAB (discussed below) which ablate material from a solid surface are less suited to chromatographic separations. For most purposes, it has been very costly to link a chromatographic separation in-line with mass spectrometric analysis by one of these techniques. Dynamic FAB and ionisation techniques based on spraying such as electrospray, and APCI are all readily compatible with in-line chromatographic separations and equipment to perform such liquid chromatography mass spectrometry analysis is commercially available.

Ionisation Techniques

For many biological mass spectrometry applications so called 'soft' ionisation techniques are used. These allow large molecules such as proteins and nucleic acids to be ionised essentially intact. The liquid phase techniques allow large biomolecules to enter the mass spectrometer in solutions with mild pH and at low concentrations. A number of techniques are appropriate for use with this invention including but not limited to Electrospray Ionisation Mass Spectrometry (ESI-MS), Fast Atom Bombardment Matrix Assisted Laser Desorption Ionisation Mass Spectrometry (MALDI MS) and Atmospheric Pressure Chemical Ionisation Mass Spectrometry (APCI-MS).

Electrospray Ionization

Electrospray ionisation requires that the dilute solution of the analyte molecule is the spectrometer, i.e. injected as a fine spray. The solution is, for example, sprayed from the tip of a charged needle in a stream of dry nitrogen and an electrostatic field. The mechanism of ionisation is not fully understood but is thought to work broadly as follows. In a stream of nitrogen the solvent is evaporated. With a small droplet, this results in concentration of the analyte molecule. Given that most biomolecules have a net charge this increases the electrostatic repulsion of the dissolved molecule. As evaporation continues this repulsion ultimately becomes greater than the surface tension of the droplet and the droplet disintegrates into smaller droplets. This process is sometimes referred to as explosion'. The electrostatic field helps to further overcome the surface tension of the droplets and assists in the spraying process. The evaporation continues from the smaller droplets which, in turn, explode iteratively until essentially the biomolecules are in the vapour phase, as is all the solvent. This technique is of particular importance in the use of mass labels in that the technique imparts a relatively small amount of energy to ions in the ionisation process and the energy distribution within a population tends to fall in a narrower range when compared with other techniques. The ions are accelerated out of the ionisation chamber by the use of electric fields that are set up by appropriately positioned electrodes. The polarity of the fields may be altered to extract either negative or positive ions. The potential difference between these electrodes determines whether positive or negative ions pass into the mass analyser and also the kinetic energy with which these ions enter the mass spectrometer. This is of significance when considering fragmentation of ions in the mass spectrometer. The more energy imparted to a population of ions the more likely it is that fragmentation will occur through collision of analyte molecules with the bath gas present in the source. By adjusting the electric field used to accelerate ions from the ionisation chamber it is possible to control the fragmentation of ions. This is advantageous when fragmentation of ions is to be used as a means of removing tags from a labelled biomolecule. Electrospray ionisation is particularly advantageous as it can be used in-line with liquid chromatography, referred to as Liquid Chromatography Mass Spectrometry (LC-MS).

Matrix Assisted Laser Desorption Ionisation (MALDI)

MALDI requires that the biomolecule solution be embedded in a large molar excess of a photo-excitable 'matrix'. The application of laser light of the appropriate frequency results in the excitation of the matrix which in turn leads to rapid evaporation of the matrix along with its entrapped biomolecule. Proton transfer from the acidic matrix to the biomolecule gives rise to protonated forms of the biomolecule which can be detected by positive ion mass spectrometry, particularly by mass spectrometry. Negative ion mass spectrometry is also possible by MALDI TOF. This technique imparts a significant quantity of translational energy to ions, but tends not to induce excessive fragmentation despite this. Accelerating voltages can again be used to control fragmentation with this technique though. This technique is highly favoured for the determination of peptide mass fingerprints due to its large mass range, due to the prevalence of singly charged ions in its spectra and due to the ability to analyse multiple peptides simultaneously.

Fast Atom Bombardment

Fast Atom Bombardment (FAB) has come to describe a number of techniques for vaporising and ionising relatively involatile molecules. In these a sample is desorbed from a surface by collision of the sample with a high energy beam of xenon atoms or caesium ions. The sample is coated onto a surface with a simple matrix, typically a non volatile material, e.g. m-nitrobenzyl alcohol (NBA) or glycerol. FAB techniques are also compatible with liquid phase inlet systems—the liquid eluting from a capillary electrophoresis inlet or a high pressure liquid chromatography system pass through a frit, essentially coating the surface of the frit with analyte solution which can be ionised from the frit surface by atom bombardment.

Mass Analysers

Fragmentation of peptides by collision induced dissociation, to determine their sequence, may be used in this invention to identify proteins, not identified by the pattern of masses of their digestion products. Various mass analyser geometries may be used to fragment peptides and to determine the mass of the fragments.

MS/MS and $MS^n$ Analysis of Proteins

Tandem mass spectrometers allow ions with a pre-determined mass-to-charge ratio to be selected and fragmented by collision induced dissociation (CID). The fragments can then be detected providing structural information about the selected ion. When peptides are analysed by CID in a tandem mass spectrometer, characteristic cleavage patterns are observed, which allow the sequence of the peptide to be determined. Natural peptides typically fragment randomly at the amide bonds of the peptide backbone to give series of ions that are characteristic of the peptide. CID fragment series are denoted etc. for cleavage at the peptide bond where the charge of the ion is retained on the N-terminal fragment of the ion. Similarly, fragment series are denoted y, zn, etc. where the charge is retained on the C-terminal fragment of the ion.

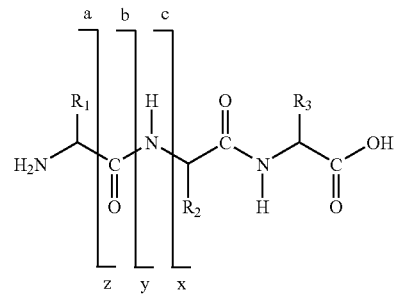

Trypsin, Lys-C and thrombin are favoured cleavage agents for tandem mass spectrometry as they produce peptides with basic groups at both ends of the molecule, i.e. the alpha-amino group at the N-terminus and lysine or arginine side-chains at the C-terminus. This favours the formation of doubly charged ions, in which the charged centres are at opposite termini of the molecule. These doubly charged ions produce both C-terminal and N-terminal ion series after CID. This assists in determining the sequence of the peptide. Generally speaking only one or two of the possible ion series are observed in the CID spectra of a given peptide. In low-energy collisions typical of quadrupole based instruments the b-series of N-terminal fragments or the y-series of C-terminal fragments predominate. If doubly charged ions are analysed then both series are often detected. In general, the y-series ions predominate over the In general peptides fragment via a mechanism that involves protonation of the amide backbone follow by intramolecular nucleophilic attack leading to the formation of a 5-membered oxazolone structure and cleavage of the amide linkage that was protonated (Schlosser A. and Lehmann W. J. Mass Spectrom. 35: ring formation in unimolecular reactions of peptides: a key structural element controlling low-energy collision induced dissociation", 2000). FIG. 16a shows one proposed mechanism by which this sort of fragmentation takes place. This mechanism requires a carbonyl group from an amide bond adjacent to a protonated amide on the N-terminal side of the protonated amide to carry out the nucleophilic attack. A charged oxazolonium ion gives rise to b-series ions, while proton transfer from the N-terminal fragment to the C-terminal fragment gives rise to y-series ions as shown in FIG. 16a. This requirement for an appropriately located carbonyl group does not account for cleavage at amide bonds adjacent to the N-terminal amino acid, when the N-terminus is not protected and, in general, b-series ions are not seen for the amide between the N-terminal and second amino acid in a peptide. However, peptides with acetylated N-termini do meet the structural requirements of this mechanism and fragmentation can take place at the amide bond immediately after the first amino acid by this mechanism.

The ease of fragmentation of the amide backbone of a polypeptide or peptide is also significantly modulated by the side chain functionalities of the peptide. Thus the sequence of a peptide determines where it will fragment most easily. In general it is difficult to predict which amide bonds will fragment easily in a peptide sequence. This has important consequences for the design of the peptide mass tags of this invention. However, certain observations have been made that allow peptide mass tags that fragment at the desired amide bond to be designed. Proline, for example, is known to promote fragmentation at its N-terminal amide bond (Schwartz B. L., Bursey M. M., Biol. Mass Spectrom. 21: 92, 1997) as fragmentation at the C-terminal amide gives rise to an energetically unfavourable strained bicyclic oxazolone structure. acid also promotes fragmentation at its N-terminal amide bond. Asp-Pro linkages, however, are particularly labile in low energy CID analysis (Wysocki V. H. et al., J Mass Spectrom 35 (12): 1399–1406, "Mobile and localized protons: a framework for understanding peptide dissociation." 2000) and in this situation aspartic acid seems to promote the cleavage of the amide bond on its C-terminal side.

A typical tandem mass spectrometer geometry is a triple quadrupole which comprises two quadrupole mass analysers separated by a collision chamber, also a quadrupole. This collision quadrupole acts as an ion guide between the two mass analyser quadrupoles. A gas can be introduced into the collision quadrupole to allow collision with the ion stream from the first mass analyser. The first mass analyser selects ions on the basis of their mass/charge ration which pass through the collision cell where they fragment. The fragment ions are separated and detected in the third quadrupole. Induced cleavage can be performed in geometries other than tandem analysers. Ion trap mass spectrometers can promote fragmentation through introduction of a gas into the trap itself with which trapped ions will collide. Ion traps generally contain a bath gas, such as helium but addition of neon for example, promotes fragmentation. Similarly photon induced fragmentation could be applied to trapped ions. Another favorable geometry is a Time of Flight tandem instrument where the high scanning rate of a quadrupole is coupled to the greater sensitivity of a reflectron TOF mass analyser to identify the products of fragmentation.

Conventional 'sector' instruments are another common geometry used in tandem mass spectrometry. A sector mass analyser comprises two separate 'sectors', an electric sector which focuses an ion beam leaving a source into a stream of ions with the same kinetic energy using electric fields. The magnetic sector separates the ions on the basis of their mass to generate a spectrum at a detector. For tandem mass spectrometry a two sector mass analyser of this kind can be used where the electric sector provide the first mass analyser stage, the magnetic sector provides the second mass analyser, with a collision cell placed between the two sectors. Two complete sector mass analysers separated by a collision cell can also be used for analysis of mass tagged peptides.

Ion Traps

Ion Trap mass analysers are related to the quadrupole mass analysers. The ion trap generally has a 3 electrode construction—a cylindrical electrode with 'cap' electrodes at each end forming a cavity. A sinusoidal radio frequency potential is applied to the cylindrical electrode while the cap electrodes are biased with DC or AC potentials. Ions injected into the cavity are constrained to a stable circular trajectory by the oscillating electric field of the cylindrical electrode. However, for a given amplitude of the oscillating potential, certain ions will have an unstable trajectory and will be ejected from the trap. A sample of ions injected into the trap can be sequentially ejected from the trap according to their mass/charge ratio by altering the oscillating radio frequency potential. The ejected ions can then be detected allowing a mass spectrum to be produced.

Ion traps are generally operated with a small quantity of a 'bath such as helium, present in the ion trap cavity. This increases both the resolution and the sensitivity of the device as the ions entering the trap are essentially cooled to the ambient temperature of the bath gas through collision with the bath gas. Collisions both increase ionisation when a sample is introduced into the trap and dampen the amplitude and velocity of ion trajectories keeping them nearer the centre of the trap. This means that when the oscillating potential is changed, ions whose trajectories become unstable gain energy more rapidly, relative to the damped circulating ions and exit the trap in a tighter bunch giving a narrower larger peaks.

Ion traps can mimic tandem mass spectrometer geometries, in fact they can mimic multiple mass spectrometer geometries allowing complex analyses of trapped ions. A single mass species from a sample can be retained in a trap, i.e. all other species can be ejected and then the retained species can be carefully excited by super-imposing a second oscillating frequency on the first. The excited ions will then collide with the bath gas and will fragment if sufficiently excited. The fragments can then be analysed further. It is possible to retain a fragment ion for further analysis by ejecting other ions and then exciting the fragment ion to fragment. This process can be repeated for as long as sufficient sample exists to permit further analysis. It should be noted that these instruments generally retain a high proportion of fragment ions after induced fragmentation. These instruments and FTICR mass spectrometers (discussed below) represent a form of temporally resolved tandem mass spectrometry rather than spatially resolved tandem mass spectrometry which is found in linear mass spectrometers.

Fourier Transform Ion Cyclotron Resonance Mass Spectrometry (FTICR MS)

Fourier FTICR mass spectrometry has similar features to ion traps in that a sample of ions is retained within a cavity but in FTICR MS the ions are trapped in a high vacuum chamber by crossed electric and magnetic fields. The electric field is generated by a pair of plate electrodes that form two sides of a box. The box is contained in the field of a superconducting magnet which in conjunction with the two plates, the trapping plates, constrain injected ions to a circular trajectory between the trapping plates, perpendicular to the applied magnetic field. The ions are excited to larger orbits by applying a radio-frequency pulse to two 'transmitter plates' which form two further opposing sides of the box. The cycloidal motion of the ions generate corresponding electric fields in the remaining two opposing sides of the box which comprise the 'receiver plates'. The excitation pulses excite ions to larger orbits which decay as the coherent motions of the ions is lost through collisions. The corresponding signals detected by the receiver plates are converted to a mass spectrum by Fourier Transform (FT) analysis.

For induced fragmentation experiments these instruments can perform in a similar manner to an ion trap-all ions except a single species of interest can be ejected from the trap. A collision gas can be introduced into the trap and fragmentation can be induced. The fragment ions can be subsequently analysed. Generally fragmentation products and bath gas combine to give poor resolution if analysed by FT analysis of signals detected by the 'receiver plates', however the fragment ions can be ejected from the cavity and analysed in a tandem configuration with a quadrupole, for example.

EXAMPLES

Example 1

Labelling Conditions for Thiol and Epsilon Amino Group Labelling

Since most proteins typically have one or more cysteine residues, which may be cross-linked to form disulphide bridges, and since thiol groups of cysteine are the most reactive side-chains in a polypeptide, it is essential that protocols are found that block this functionality as well as any free epsilon amino groups. The hindered Michael reagents used in this invention will react readily with thiols as well as with epsilon amino groups and so both functionalities may be labelled in a single reaction.

Alternatively the thiols may be labelled with a different reagent prior to labelling the epsilon amino groups with the hindered Michael reagents of this invention.

Capping Thiol and Epsilon Amino Groups with Different Tags

In this example salmon Calcitonin (10° nmol, Calbiochem), which has 2 cysteine residues in a disulphide bridge, was dissolved in a denaturing buffer comprising 2 M urea, 0.5 M thiourea in carbonate at pH 7.5 in the presence of 0.2 phosphine TCEP reduces disulphide bridges. The reaction mixture also contained (20 equivalent per thiol site, 400 nmol) which reacts readily with free thiols. This reaction was left for 90 min. at room temperature. The pH of the buffer was then raised to between 10 and 12 by the addition of sodium hydroxide. Pyridyl propenyl sulphone was then added to the reaction to cap free lysine residues in Salmon Calcitonin. This peptide has 2 lysine residues. The reaction was then desalted (Oasis hydrophilic-lipophilic balance extraction cartridge, Waters) and analysed by MALDI TOF mass spectrometry. The mass spectrum is shown in FIG. 7. As can be seen from this mass spectrum a number of different species appear in the mass spectrum corresponding to different labelling products of the peptide. The two different labels give rise to different combinations of incomplete reactions.

Capping Thiol and Epsilon Amino Groups with the Same Tag on One Peptide

In this Example, 10 nmol of human Calcitonin was dissolved in a denaturing buffer comprising urea, 0.5M thiourea in 10 mM sodium carbonate at 5 in the presence of 0.2 uM tris(carboxyethyl) phosphine TCEP reduces disulphide bridges. This reaction was left for 30 minutes to allow complete reduction of all disulphide bridges to take place. After the reduction reaction 40 equivalents of pyridyl propenyl sulphone per reaction site, which were assumed only to comprise epsilon amino groups and thiol groups, was added to the reaction mixture. This reaction was left for 90 min. at room temperature at pH 8. The pH of the buffer was then raised to between 11–12 by the addition of sodium hydroxide. The reaction mixture was left at the higher pH for 4 hours at room temperature to cap free lysine residues in the peptides. Unreacted tag was quenched with an excess of lysine. The reaction was then desalted (Oasis hydrophilic-lipophilic balance extraction cartridge, Waters) and analysed by MALDI TOF mass spectrometry. The mass spectrum is shown in FIG. 8. As can be seen from this mass spectrum the number of different species appearing in the mass spectrum corresponding to different labelling products of each peptide is much smaller than for the protocol using two different tags for thiols and epsilon amino groups.

Capping Thiol and Epsilon Amino Groups with the Same Tag on a Mixture of Peptides In this Example, a mixture of peptides of each) comprising beta-melanocyte stimulating hormone (B-MSH), alpha-melanocyte stimulating hormone (a-MSH), Salmon Calcitonin and residues 1 to 24 of adrenocorticotropic hormone (ACTH (1–24)) (all available from Sigma-Aldrich, Dorset, UK) were dissolved in a denaturing buffer comprising 2 M urea, 0.5 M thiourea in 10 mM sodium borate at pH 7.5 in the presence of 0.2, uM TCEP. This reaction was left for 30 minutes to allow complete reduction of all disulphide bridges to take place. After the reduction reaction 40 equivalents of pyridyl propenyl sulphone per reaction site, which were assumed only to comprise epsilon amino groups and thiol groups, was added to the reaction mixture. This reaction was left for 90 min. at room temperature at pH 8. The pH of the buffer was then raised to between 11–12 by the addition of sodium hydroxide. The reaction mixture was left at the higher pH for 4 hours at room temperature to cap free lysine residues in the peptides. Unreacted tag was quenched with an excess of lysine. The reaction was then desalted (Oasis hydrophilic-lipophilic balance extraction cartridge, Waters) and analysed by MALDI TOF mass spectrometry. The mass spectrum is shown in FIG. 9. As can be seen from this mass spectrum the number of different species appearing in the mass spectrum corresponding to different labelling products of each peptide is much smaller than for the protocol using two different tags for thiols and epsilon amino groups.

Capping of Unblocked Alpha Amino Groups

Following the capping of the mixture of peptides above, the unblocked alpha-amino groups were blocked with acetic acid N-hydroxysuccinimide ester. The thiol and epsilon amino capped peptides were exposed to 40 equivalents of the active ester reagent per alpha amino group in the same sodium borate buffer used previously at pH 11 for 2 hours at room temperature. The MALDI TOF mass spectrum of the products of this reaction is shown in FIG. 10. As can be seen from this figure, only one acetyl group reacts with each of the peptides that are expected to react, i.e. all of the four peptides except This means that the capped epsilon amino groups are resistant to reaction with the active ester reagent.

The invention claimed is:

1. A method for determining the identity of a polypeptide, which method comprises the steps of:
    (a) optionally reducing cysteine disulphide bridges in the polypeptide to form free thiols, and capping the free thiols;
    (b) cleaving the polypeptide with a sequence specific cleavage reagent to form peptide fragments;
    (c) optionally deactivating the cleavage reagent;
    (d) capping one or more ε-amino groups that are present with a lysine reactive agent, wherein the lysine reactive agent comprises a hindered Michael reagent;
    (e) analyzing peptide fragments by mass spectrometry to determine a peptide mass fingerprint for the polypeptide; and
    (f) determining the identity of the polypeptide from the peptide mass fingerprints;
    wherein the hindered Michael agent comprises a compound having the following structure:

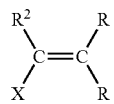

wherein X is an electron withdrawing group that stabilizes a negative charge; the R groups independently comprise a hydrogen, a halogen, an alkyl, an aryl, or an aromatic group with the proviso that at least one of the R groups comprises a sterically hindering group; and the group $R^2$ comprises a hydrogen, a halogen, a hydrocarbon group, an electron withdrawing group and/or a linker that attaches to an affinity capture functionality or a solid phase support.

2. The method according to claim 1, wherein the lysine-reactive agent is a labeled lysine-reactive agent.

3. The method according to claim 1, wherein the sequence specific cleavage agent cleaves the one or more polypeptides on the C-terminal side of a lysine residue.

4. The method according to claim 1, wherein the specific cleavage reagent comprises Lys-C or Trypsin.

5. The method according to claim 1, wherein the peptide fragments having capped ε-amino groups are removed by affinity capture, and wherein the lysine reactive agent comprises biotin.

6. The method according to claim 1, wherein one R comprises a methyl or phenyl group.

7. The method according to claim 1, wherein at least one R comprises an electron withdrawing group.

8. The method according to claim 1, wherein at least one R comprises a cyclic or heterocylic aromatic ring or fused ring.

9. The method according to claim 1, wherein X comprises an —$SO_2R^1$ group, wherein $R^1$ comprises an alkyl group or an aryl group, including aromatic groups, cyclic groups, fused cyclic groups, and heterocyclic groups.

10. The method according to claim 9, wherein $R^1$ comprises an electron withdrawing group.

11. The method according to claim 9, wherein $R^1$ comprises a phenyl, pyridyl, naphthyl, quinolyl, pyrazine, pyrimidine or triazine ring structure.

12. The method according to claim 1 wherein the X group is substituted with an electron withdrawing group.

13. The method according to claim 12, wherein the electron withdrawing group is selected from halogens, such as fluorine chlorine, bromine or iodine, and nitro and nitrile groups.

14. The method according to claim 1, wherein the X group comprises a structure that promotes water solubility.

15. The method according to claim 1, wherein the polypeptide is isolated from a sub-cellular compartment.

16. The method according to claim 1, which further comprises preparing the polypeptide by liquid chromatography.

17. A method for determining the identity of one or more polypeptides in a sample comprising a population of polypeptides, which method comprises the steps of:
    (a) optionally reducing cysteine disulphide bridges in one or more of the polypeptides to form free thiols, and capping the free thiols;
    (b) separating one or more of the polypeptides from the sample;
    (c) cleaving the one or more polypeptides with a sequence specific cleavage reagent to form peptide fragments;
    (d) optionally deactivating the cleavage reagent;
    (e) capping one or more ε-amino groups that are present with a lysine reactive agent, wherein the lysine reactive agent comprises a hindered Michael reagent;
    (f) analyzing the peptide fragments by mass spectrometry to form a peptide mass fingerprint for the one or more polypeptides; and
    (g) determining the identity of the one or more polypeptides from the peptide mass fingerprint;
    wherein the hindered Michael agent comprises a compound having the following structure:

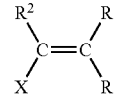

wherein X is an electron withdrawing group that stabilizes a negative charge; the R groups independently comprise a hydrogen a halogen, an alkyl, an aryl, or an aromatic group with the proviso that at least one of the R groups comprises a sterically hindering group; and the group $R^2$ comprises a hydrogen, a halogen, a hydrocarbon group, an electron withdrawing group and/or a linker that attaches to an affinity capture functionality or a solid phase support.

18. The method according to claim 17, wherein the identity of the one or more polypeptides is determined by assaying the one or more mass fingerprints for a predetermined peptide mass fingerprint.

19. The method according to claim 17, wherein the peptide mass fingerprints are used to determine an expression profile in the sample.

20. The method according to claim 19, which method comprises identifying the quantity of each of the one or more polypeptides that was present in each of the samples.

21. A method for comparing peptide mass fingerprints for a plurality of samples, each sample comprising one or more polypeptides, which method comprises the steps of:

(a) optionally reducing cysteine disulphide bridges and capping the free thiols in one or more polypeptides from each of the samples;
(b) separating one or more polypeptides from each of the samples;
(c) cleaving the one or more polypeptides with a sequence specific cleavage reagent to form peptide fragments;
(d) optionally deactivating the cleavage reagent;
(e) capping one or more $\epsilon$-amino groups that are present with a lysine reactive agent, wherein the lysine reactive agent comprises a hindered Michael reagent;
(f) analyzing the peptide fragments by mass spectrometry to form a peptide mass fingerprints for the one or more polypeptides; and
(g) determining the identity of the one or more polypeptides from the peptide mass fingerprints; and
(h) comparing the peptide mass fingerprints of the plurality of samples;

wherein the hindered Michael agent comprises a compound having the following structure:

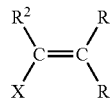

wherein X is an electron withdrawing group that stabilizes a negative charge; the R groups independently comprise a hydrogen, a halogen, an alkyl an aryl, or an aromatic group with the proviso that at least one of the R groups comprises a sterically hindering group; and the group $R^2$ comprises a hydrogen a halogen, a hydrocarbon group, an electron withdrawing group and/or a linker that attaches to an affinity capture functionality or a solid phase support.

22. The method according to claim 21, which method comprises the steps of:
(a) optionally reducing cysteine disulphide bridges and capping the free thiols in one or more polypeptides from each of the samples;
(b) capping one or more $\epsilon$-amino groups that are present in each sample with a labeled lysine reactive agent;
(c) pooling the samples;
(d) separating one or more polypeptides from the pooled samples;
(e) cleaving the one or more polypeptides with a sequence specific cleavage reagent to form peptide fragments;
(f) optionally deactivating the cleavage reagent;
(g) analyzing the peptide fragments by mass spectrometry to form a peptide mass fingerprint for the one or more polypeptides; and
(h) determining the identity of the one or more polypeptides from the peptide mass fingerprints,
wherein the same label is employed for polypeptides or peptides from the same sample, and different labels are employed for polypeptides or peptides from different samples, such that the sample from which a polypeptide or peptide originates can be determined from its label.

* * * * *